United States Patent
Ran et al.

(10) Patent No.: US 12,428,431 B2
(45) Date of Patent: Sep. 30, 2025

(54) ORGANIC COMPOUND, ELECTROLUMINESCENT MATERIAL, AND USE THEREOF

(71) Applicants: WUHAN TIANMA MICROELECTRONICS CO., LTD., Wuhan (CN); WUHAN TIANMA MICROELECTRONICS CO., LTD. SHANGHAI BRANCH, Shanghai (CN)

(72) Inventors: Quan Ran, Wuhan (CN); Wei Gao, Wuhan (CN); Lei Zhang, Wuhan (CN)

(73) Assignees: WUHAN TIANMA MICROELECTRONICS CO., LTD., Wuhan (CN); WUHAN TIANMA MICROELECTRONICS CO., LTD. SHANGHAI BRANCH, Shanghai (CN)

( * ) Notice: Subject to any disclaimer, the term of this patent is extended or adjusted under 35 U.S.C. 154(b) by 885 days.

(21) Appl. No.: 17/544,946

(22) Filed: Dec. 8, 2021

(65) Prior Publication Data

US 2022/0098213 A1    Mar. 31, 2022

(30) Foreign Application Priority Data

Jul. 26, 2021    (CN) .......................... 202110843070.3

(51) Int. Cl.
*C07D 493/10*    (2006.01)
*C07D 493/00*    (2006.01)
(Continued)

(52) U.S. Cl.
CPC ......... *C07D 493/10* (2013.01); *C07D 493/00* (2013.01); *C07D 495/00* (2013.01);
(Continued)

(58) Field of Classification Search
CPC .. C07D 493/00; C07D 495/00; C07D 498/04; C07D 519/00; C07D 491/107;
(Continued)

(56) References Cited

U.S. PATENT DOCUMENTS

2014/0225040 A1*    8/2014    Parham ............... C07F 9/65685
544/70

FOREIGN PATENT DOCUMENTS

| CN | 105001229 A | * 10/2015 | ........... C07D 493/10 |
| CN | 106187861 A | 12/2016 | |

(Continued)

OTHER PUBLICATIONS

Machine Translation of KR20170141989 (Year: 2017).*

(Continued)

*Primary Examiner* — Jenna N Chandhok
(74) *Attorney, Agent, or Firm* — KILPATRICK TOWNSEND & STOCKTON LLP

(57) ABSTRACT

Provided are an organic compound, an electroluminescent material and use thereof. The organic compound has a structure as shown in Formula I. Through the molecular structure design, the organic compound has a deep LUMO energy level, which can reduce electron injection potential barrier and improve electron injection ability; it has a deep HOMO, which can effectively block holes and make more electron-holes recombine in the light-emitting layer; it has a high triplet energy level $E_{T1}$, which can effectively block light-emitting layer excitons. The molecule has a twisted spiro structure, which can reduce molecules stacking, avoid crystallization, show excellent thermal stability and film stability, and help improve luminous efficiency and lifetime. As electroluminescent materials, the organic compound is suitable for an electron transport layer and/or a hole blocking layer of OLED devices and can reduce voltage and (Continued)

power consumption, improve luminous efficiency and working lifetime to have better comprehensive performance.

16 Claims, 1 Drawing Sheet

(51) Int. Cl.

| | | |
|---|---|---|
| C07D 495/00 | (2006.01) | |
| C07D 498/04 | (2006.01) | |
| C07D 519/00 | (2006.01) | |
| H10K 50/11 | (2023.01) | |
| H10K 50/16 | (2023.01) | |
| H10K 50/18 | (2023.01) | |
| H10K 85/60 | (2023.01) | |
| H10K 101/10 | (2023.01) | |
| H10K 101/30 | (2023.01) | |
| H10K 101/40 | (2023.01) | |

(52) U.S. Cl.
CPC ......... *C07D 498/04* (2013.01); *C07D 519/00* (2013.01); *H10K 85/615* (2023.02); *H10K 85/654* (2023.02); *H10K 85/6572* (2023.02); *H10K 85/6574* (2023.02); *H10K 85/6576* (2023.02); *H10K 50/11* (2023.02); *H10K 50/16* (2023.02); *H10K 50/18* (2023.02); *H10K 2101/10* (2023.02); *H10K 2101/30* (2023.02); *H10K 2101/40* (2023.02)

(58) Field of Classification Search
CPC .. C07D 495/10; C07D 493/10; H10K 85/615; H10K 85/654; H10K 85/6572; H10K 85/6574; H10K 85/6576; H10K 85/657
See application file for complete search history.

(56) References Cited

FOREIGN PATENT DOCUMENTS

| | | | | |
|---|---|---|---|---|
| CN | 109970660 A | * | 7/2019 | |
| CN | 112694481 A | * | 4/2021 | ......... C07D 491/107 |
| KR | 20150113642 A | | 10/2015 | |
| KR | 2017141989 A | * | 12/2017 | ........... C07D 307/94 |
| WO | 2014010910 A1 | | 1/2014 | |

OTHER PUBLICATIONS

Machine Translation of CN109970660A (Year: 2019).*
Machine Translation of CN112694481A (Year: 2021).*
Machine Translation of CN105001229A (Year: 2018).*

* cited by examiner

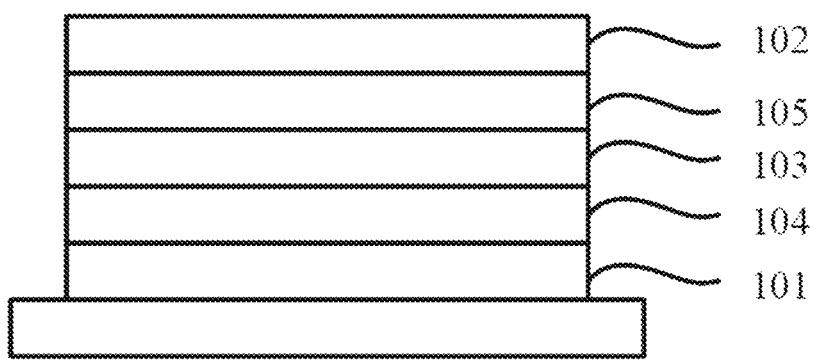

ORGANIC COMPOUND, ELECTROLUMINESCENT MATERIAL, AND USE THEREOF

CROSS-REFERENCE TO RELATED APPLICATIONS

The application claims the benefit of the earlier filing date of Chinese Patent Application No. CN202110843070.3, filed on Jul. 26, 2021 to the China National Intellectual Property Administration (CNIPA), the contents of which are incorporated by reference herein in its entirety.

FIELD

The present disclosure belongs to the field of organic electroluminescent materials, and specifically, relates to an organic compound, an electroluminescent material, and use thereof.

BACKGROUND

Organic electroluminescence technology is one of the most promising emerging technologies in the field of optoelectronics. Compared with inorganic light-emitting diodes, organic light-emitting diodes (OLEDs) have the advantages such as self-luminescence, low power consumption, high contrast, wide color gamut, flexibility, and foldability, and thus have attracted wide attention from researchers and enterprise researchers. The OLEDs have been successfully applied in business and have been widely used in various industries such as flexible display, flat panel display, and solid-state lighting.

The OLED device usually has a sandwich-like stacked structure including a cathode, an anode, and multiple organic film layers sandwiched between the two electrodes, and the organic film layers include a light-emitting layer and other functional layers such as an electron transport layer, a hole transport layer, a hole injection layer, and an electron injection layer to assist transmission. When a voltage is applied across two electrodes of an OLED device, holes generated from the anode and electrons generated from the cathode are injected into the light-emitting layer and recombine in the light-emitting layer to form excitons, and the excitons emit light when the excitons change from the excited state to the ground state. Therefore, in the OLED device, the materials and properties of organic film layers have a very important influence on the luminescence properties of devices.

The electron transport material used in conventional OLED devices is 8-hydroxyquinoline aluminum ($Alq_3$), but the electron mobility of $Alq_3$ is low (about $10^{-6}$ $cm^2/Vs$), which causes the imbalance between electron transport and hole transport. With the commercialization and application of electroluminescent devices, people hope to obtain electron transport materials with higher transport efficiency and better performance. In this field, researchers have conducted a lot of exploratory work.

WO2007011170A discloses an imidazole derivative and organic electronic device using the same. The imidazole derivative has a skeleton structure of naphthoimidazole, and different types of substituents are attached to the skeleton structure, and the molecule exhibits strong p-type or n-type and the imidazole derivative can be used in materials for electron transport, electron injection, hole transport, and hole injection. In an electron transport compound and an organic light-emitting diode including the same disclosed in CN101003508A, a series of pyrene-based electron transport compounds are designed, which shows good electron transport efficiency and deposition characteristics. US20060204784A and US20070048545A of KODAK CO disclose an organic electroluminescent device with a mixed electron transport material, where the mixed electron transport material is formed by doping with the following materials: (a) a first compound having the lowest LUMO level in the layer, (b) a second compound having a higher LUMO level than the first compound and having a low turn-on voltage, and a metal material having a work function less than 4.2 eV. However, the above-mentioned electron transport materials have a planar molecular structure and a large intermolecular attraction force, which is not helpful for evaporation and application; moreover, these electron transport materials still have some defects such as low mobility, poor energy level aligning, poor thermal stability, short service life, being doped and so on, which limit the further development of OLED display devices.

With the development of OLED display technology, many current electron transport materials commercially available, such as batho-phenanthroline

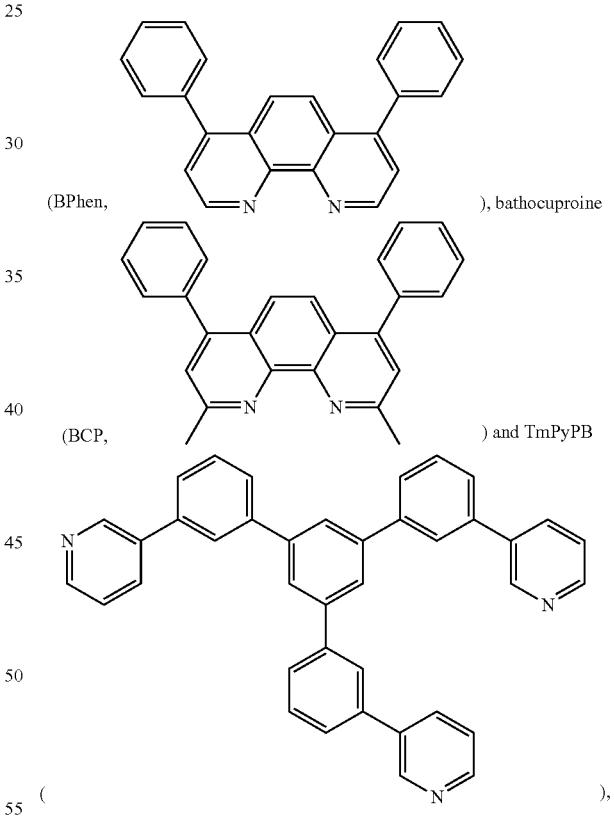

can generally satisfy the market demand for organic electroluminescent panels, but have a low glass transition temperature which is generally lower than 85° C., and when the devices including the same are operating, generated Joule heat causes molecular degradation and changes in molecular structure, resulting in low panel efficiency and poor thermal stability. Meanwhile, the molecular structure of these materials has a very regular symmetry, which makes these materials prone to crystallization after long-term use. Once crystallization occurs in the electron transport material, the intermolecular charge transition mechanism will differ from the mechanism of the normally operated amorphous film, and electron transport performance decreases, the electron mobility and the hole mobility of the entire device are unbalanced, exciton formation efficiency is greatly reduced, and excitons are concentrated at the interface between the electron transport layer and the light-emitting layer, resulting in the serious decrease of device efficiency and lifetime.

Therefore, it is urgent to develop more types of electron transport materials with higher performance in the art to satisfy the application requirements of OLED display devices.

SUMMARY

In order to develop more types of electron transport materials with better performance, one embodiment of the present disclosure is to provide an organic compound having a structure as shown in Formula I.

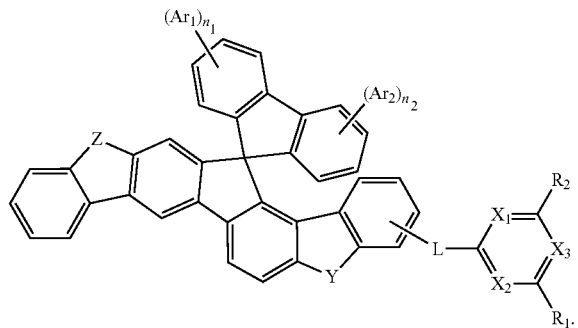

Formula I

In Formula I, $X_1$, $X_2$, and $X_3$ are each independently N or CR.

In Formula I, Y and Z are each independently selected from O, S, $NR_N$ or $CR_{C1}R_{C2}$.

In Formula I, L is selected from any one of a single bond, substituted or unsubstituted C6 to C40 arylene, or substituted or unsubstituted C3 to C40 heteroarylene, and the expression that L is a single bond is intended to mean that the six-membered ring where $X_1$ is located is directly linked to the skeleton structure through a single bond.

$R_1$, $R_2$, R, $R_N$, $R_{C1}$, and $R_{C2}$ are each independently selected from any one of hydrogen, substituted or unsubstituted C1 to C20 linear or branched alkyl, substituted or unsubstituted C6 to C40 aryl, or substituted or unsubstituted C2 to C40 heteroaryl.

In Formula I, $Ar_1$ and $Ar_2$ are each independently selected from any one of deuterium, halogen, cyano, substituted or unsubstituted C1 to C20 linear or branched alkyl, C1 to C20 alkoxy, C1 to C20 alkylthio, substituted or unsubstituted C3 to C20 cycloalkyl, substituted or unsubstituted C6 to C40 aryl, substituted or unsubstituted C2 to C40 heteroaryl, or substituted or unsubstituted C6 to C40 arylamino.

In Formula I, $n_1$ and $n_2$ are each independently selected from integers from 0 to 4 and for example, may be 0, 1, 2, 3 or 4.

In the present disclosure, C6 to C40 may each independently be C6, C9, C10, C12, C13, C14, C15, C16, C18, C20, C22, C24, C26, C28, C30, C32, C34, C36, C38, etc.

C3 to C40 may each independently be C3, C4, C5, C6, C7, C8, C9, C10, C12, C13, C14, C15, C16, C18, C20, C22, C24, C26, C28, C30, C32, C34, C36, C38, etc.

C1 to C20 may each independently be C2, C3, C4, C5, C6, C8, C10, C12, C14, C16, C18, C19, etc.

C2 to C40 may each independently be C2, C3, C4, C5, C6, C7, C8, C9, C10, C12, C13, C14, C15, C16, C18, C20, C22, C24, C26, C28, C30, C32, C34, C36, C38, etc.

C3 to C20 may each independently be C4, C5, C6, C8, C10, C11, C13, C15, C17, C19, C20, etc.

In the present disclosure, the halogen includes fluorine, chlorine, bromine or iodine. The same expression hereinafter has the same meaning.

With the coordination of the skeleton structure and the substituents, the organic compound provided by the present disclosure obtains good electron transport (ET) material characteristics which are as follows: (1) sufficiently high reduction potential, which is helpful for electron transport, reduces the potential barrier for electron injection, and further reduces the device voltage; (2) suitable HOMO and LUMO energy levels, which is helpful for the energy level matching between adjacent layers and makes the organic compound have certain hole blocking ability through a deep HOMO energy level; (3) high triplet energy level $E_{T1}$, which can effectively block excitons in the light-emitting layer and improve the luminous efficiency; (4) high thermal decomposition temperature, which leads to good thermal stability and reduces the influence of Joule heat generated when the device works on the lifetime and efficiency; (5) high glass-transition temperature, which makes the compound exhibit amorphous film morphology in the device and leads to good film formation uniformity with no pinhole; and (6) three-dimensional structure, which can reduce the crystallization caused by the stacking of molecules.

One embodiment of the present disclosure is to provide an electroluminescent material including the organic compound as described in other embodiments.

Some embodiments of the present disclosure is to provide an OLED device including an anode, a cathode, and an organic thin film layer located between the anode and the cathode, where the material of the organic thin film layer includes the electroluminescent material as described in the other embodiments.

One embodiment of the present disclosure is to provide a display device including the OLED device as described in the other embodiments.

Compared with the related art, the present disclosure has beneficial effects described below.

Through the design of the molecular structure, the organic compound provided by the present disclosure has a deep LUMO energy level, which can reduce a potential barrier for electron injection and improve an electron injection ability; the organic compound has a deep HOMO, which can effectively block holes and make more electrons and holes recombine in the light-emitting layer; the organic compound has a high triplet energy level $E_{T1}$, which can effectively block excitons in the light-emitting layer; and the organic compound has a molecule in a twisted spiro structure, which can reduce the stacking of molecules and avoid crystallization and the organic compound shows excellent thermal stability and film stability, which is helpful to improve the luminous efficiency and lifetime of devices. The organic compound, as an electroluminescent material, is especially suitable for an electron transport layer and/or a hole blocking layer of the OLED device, and can reduce the voltage and power consumption of the device, improve the luminous efficiency, prolong the working lifetime, and enable the OLED device to have better comprehensive performance.

BRIEF DESCRIPTION OF DRAWINGS

The FIGURE is a structural schematic diagram of an OLED device according to the present disclosure; and, 101 represents an anode, 102 represents a cathode, 103 represents a light-emitting layer, 104 represents a first organic thin film layer, and 105 represents a second organic thin film layer.

DETAILED DESCRIPTION

The embodiments of the present disclosure are further described below through particular embodiments. The embodiments described herein are used for a better understanding of the present disclosure and should not be construed as specific limitations to the present disclosure.

Some embodiments of the present disclosure is to provide an organic compound having a structure as shown in Formula I.

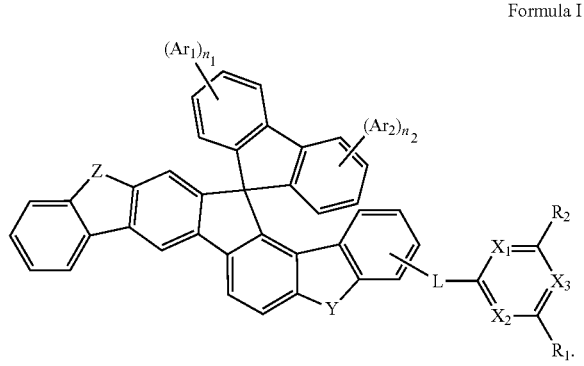

Formula I

In Formula I, $X_1$, $X_2$, and $X_3$ are each independently N or CR.

In Formula I, Y and Z are each independently selected from O, S, $NR_N$ or $CR_{C1}R_{C2}$.

In Formula I, L is selected from any one of a single bond, substituted or unsubstituted C6 to C40 arylene, or substituted or unsubstituted C3 to C40 heteroarylene, and the expression that L is a single bond is intended to mean that the six-membered ring where $X_1$ is located is directly linked to the skeleton structure through a single bond.

$R_1$, $R_2$, R, $R_N$, $R_{C1}$, and $R_{C2}$ are each independently selected from any one of hydrogen, substituted or unsubstituted C1 to C20 linear or branched alkyl, substituted or unsubstituted C6 to C40 aryl, or substituted or unsubstituted C2 to C40 heteroaryl.

In Formula I, $Ar_1$ and $Ar_2$ are each independently selected from any one of deuterium, halogen, cyano, substituted or unsubstituted C1 to C20 linear or branched alkyl, C1 to C20 alkoxy, C1 to C20 alkylthio, substituted or unsubstituted C3 to C20 cycloalkyl, substituted or unsubstituted C6 to C40 aryl, substituted or unsubstituted C2 to C40 heteroaryl, or substituted or unsubstituted C6 to C40 arylamino.

In Formula I, $n_1$ and $n_2$ are each independently selected from integers from 0 to 4, for example, may be 0, 1, 2, 3 or 4.

In the present disclosure, C6 to C40 may each independently be C6, C9, C10, C12, C13, C14, C15, C16, C18, C20, C22, C24, C26, C28, C30, C32, C34, C36, C38, etc.

C3 to C40 may each independently be C3, C4, C5, C6, C7, C8, C9, C10, C12, C13, C14, C15, C16, C18, C20, C22, C24, C26, C28, C30, C32, C34, C36, C38, etc.

C1 to C20 may each independently be C2, C3, C4, C5, C6, C8, C10, C12, C14, C16, C18, C19, etc.

C2 to C40 may each independently be C2, C3, C4, C5, C6, C7, C8, C9, C10, C12, C13, C14, C15, C16, C18, C20, C22, C24, C26, C28, C30, C32, C34, C36, C38, etc.

C3 to C20 may each independently be C4, C5, C6, C8, C10, C11, C13, C15, C17, C19, C20, etc.

In the present disclosure, the halogen includes fluorine, chlorine, bromine or iodine. The same expression hereinafter has the same meaning.

The C6 to C40 aryl involved in the present disclosure, for example, includes, but is not limited to, phenyl, biphenylyl, terphenyl, naphthyl, anthryl, phenanthryl, pyrenyl, fluorenyl and derivative groups thereof (dimethylfluorenyl, diphenylfluorenyl, and spirodifluorenyl), indenyl, perylenyl, triphenylenyl, etc.

C2 to C40 heteroaryl involved in the present disclosure, for example, includes, but is not limited to, pyridyl, pyrazinyl, pyridazinyl, pyrimidinyl, triazinyl, quinolinyl, isoquinolinyl, quinoxalinyl, quinazolinyl, pyridopyridinyl, phenanthrolinyl, acridinyl, phenazinyl, benzimidazolyl, benzothiazolyl, benzoxazoly, indolyl, furanyl, thiophenyl, pyrrolyl, dibenzofuranyl, dibenzothiophenyl, carbazolyl, N-phenylcarbazolyl, etc.

C1 to C20 linear or branched alkyl involved in the present disclosure, for example, includes, but is not limited to, methyl, ethyl, n-propyl, isopropyl, n-butyl, isobutyl, tert-butyl, n-amyl, tert-amyl, isoamyl, neopentyl, n-hexyl, n-heptyl, n-octyl, etc.

The structure of the organic compound provided by the present disclosure is as shown in Formula I and has a skeleton structure in which two groups of benzo five-membered rings are fused with spirofluorene and

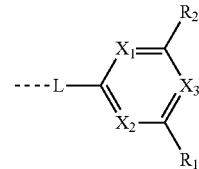

is attached to the skeleton structure. With the coordination of the skeleton structure and the substituents, the purpose of transporting electrons is achieved. The organic compound has a deep LUMO energy level (−1.70 eV to −1.97 eV), which is helpful to smoothly injecting electrons, reduces the injection potential barrier, and effectively reduces the voltage of the OLED device. The organic compound has a deep HOMO energy level (−5.41 eV to −5.48 eV), which can effectively block holes and makes more holes and electrons recombine in the light-emitting region. At the same time, the organic compound has a high triplet energy level $E_{T1}$ which is greater than or equal to 2.71 eV and can reach more than 2.90 eV, which can effectively block excitons in the light-emitting layer, improve exciton utilization rate, and further improve device efficiency. The molecule of the organic compound includes a fused spiro structure, and such a twisted structure can reduce the stacking of molecules and avoid crystallization and the organic compound is more stable in device application, has a high glass-transition temperature, and obtains excellent film stability and thermal stability.

The organic compound provided by the present disclosure, as an electroluminescent material, is especially suitable for an electron transport layer and/or a hole blocking layer of the OLED device, and can effectively improve the luminous efficiency of the device, reduce the working voltage and power consumption, and prolong the working lifetime.

In an embodiment, the substituted substituents in L, $R_1$, $R_2$, R, $R_N$, $R_{C1}$, $R_{C2}$, $Ar_1$, and $Ar_2$ are each independently selected from at least one of deuterium, cyano, halogen, unsubstituted or halogenated C1 to C10 (for example, C1, C2, C3, C4, C5, C6, C7, C8, C9 or C10) linear or branched alkyl, unsubstituted or halogenated C1 to C10 (for example, C1, C2, C3, C4, C5, C6, C7, C8, C9 or C10) alkoxy, C1 to C10 (for example, C1, C2, C3, C4, C5, C6, C7, C8, C9 or C10) alkylthio, C6 to C20 (for example, C6, C9, C10, C12, C14, C16, C18, etc.) aryl, C2 to C20 (for example, C3, C4, C5, C6, C8, C10, C12, C14, C16, C18, etc.) heteroaryl, or C6 to C18 (for example, C6, C9, C10, C12, C14, C16, C18, etc.) arylamino.

In an embodiment, at least one of $X_1$, $X_2$ or $X_3$ is N.
In an embodiment, at least two of $X_1$, $X_2$ or $X_3$ are N.
In an embodiment, $X_1$, $X_2$, and $X_3$ are all N.
In an embodiment, the organic compound has a structure as shown in Formula II-1 or Formula II-2:

Formula II-1

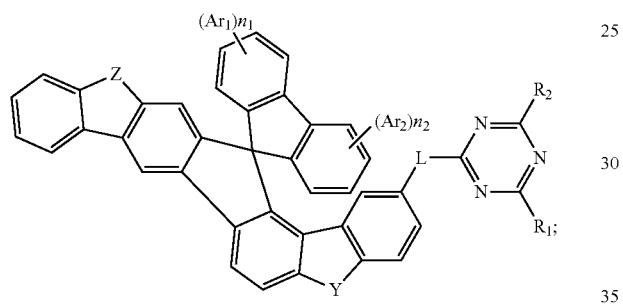

Formula II-2

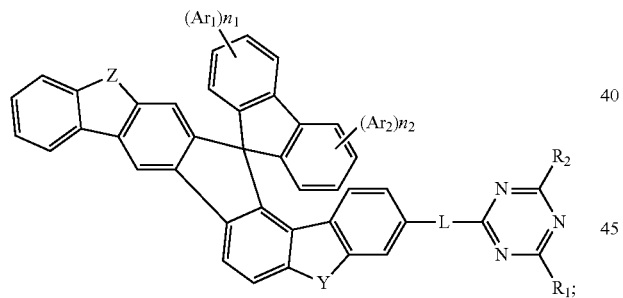

and, Y, Z, L, $R_1$, $R_2$, $Ar_1$, $Ar_2$, $n_1$, and $n_2$ have the same ranges as defined in Formula I.

In an embodiment, Y and Z are each independently selected from O, S or $NR_N$.

In an embodiment, $R_N$, $R_{C1}$, and $R_{C2}$ are each independently selected from methyl or phenyl.

In an embodiment, L is selected from any one of a single bond, phenylene, biphenylene, terphenylene, naphthylene or pyridinylene.

In an embodiment, $R_1$ and $R_2$ are each independently selected from hydrogen or any one of the following groups:

and the dashed line represents a linkage site of the group.

$L_1$ is selected from any one of a single bond or substituted or unsubstituted C6 to C20 (for example, C6, C9, C10, C12, C14, C16, C18, etc.) arylene.

$X_4$ is selected from O, S or $NR_{N1}$.

$X_5$ is selected from O, S, $NR_{N2}$ or $CR_{C3}R_{C4}$.

$R_{N1}$, $R_{N2}$, $R_{C3}$, and $R_{C4}$ are each independently selected from any one of hydrogen, substituted or unsubstituted C1 to C20 (for example, C2, C3, C4, C5, C6, C8, C10, C12, C14, C16, C18, C19, etc.) linear or branched alkyl, substituted or unsubstituted C6 to C20 (for example, C6, C9, C10, C12, C14, C16, C18, etc.) aryl, or substituted or unsubstituted C2 to C20 (for example, C3, C4, C5, C6, C8, C10, C12, C14, C16, C18, etc.) heteroaryl.

$R_{11}$ and $R_{12}$ are each independently selected from any one of deuterium, cyano, halogen, unsubstituted or halogenated C1 to C10 (for example, C1, C2, C3, C4, C5, C6, C7, C8, C9 or C10) linear or branched alkyl, unsubstituted or halogenated C1 to C10 (for example, C1, C2, C3, C4, C5, C6, C7, C8, C9 or C10) alkoxy, C1 to C10 (for example, C1, C2, C3, C4, C5, C6, C7, C8, C9 or C10) alkylthio, C6 to C20 (for example, C6, C9, C10, C12, C14, C16, C18, etc.) aryl, C2 to C20 (for example, C3, C4, C5, C6, C8, C10, C12, C14, C16, C18, etc.) heteroaryl, or C6 to C18 (for example, C6, C9, C10, C12, C14, C16, C18, etc.) arylamino.

$m_1$ is selected from integers from 0 to 5 and, for example, may be 0, 1, 2, 3, 4 or 5.

$m_2$ is selected from integers from 0 to 6 and for example, may be 0, 1, 2, 3, 4, 5 or 6.

$m_3$ is selected from integers from 0 to 9 and for example, may be 0, 1, 2, 3, 4, 5, 6, 7, 8 or 9.

$m_4$ and $m_6$ are each independently selected from integers from 0 to 4 and, for example, may be 0, 1, 2, 3 or 4.

$m_5$ is selected from integers from 0 to 3 and for example, may be 0, 1, 2 or 3.

In an embodiment, $R_1$ and $R_2$ are each independently selected from hydrogen, or any one of the following groups, or any one of the following groups substituted with a substituent:

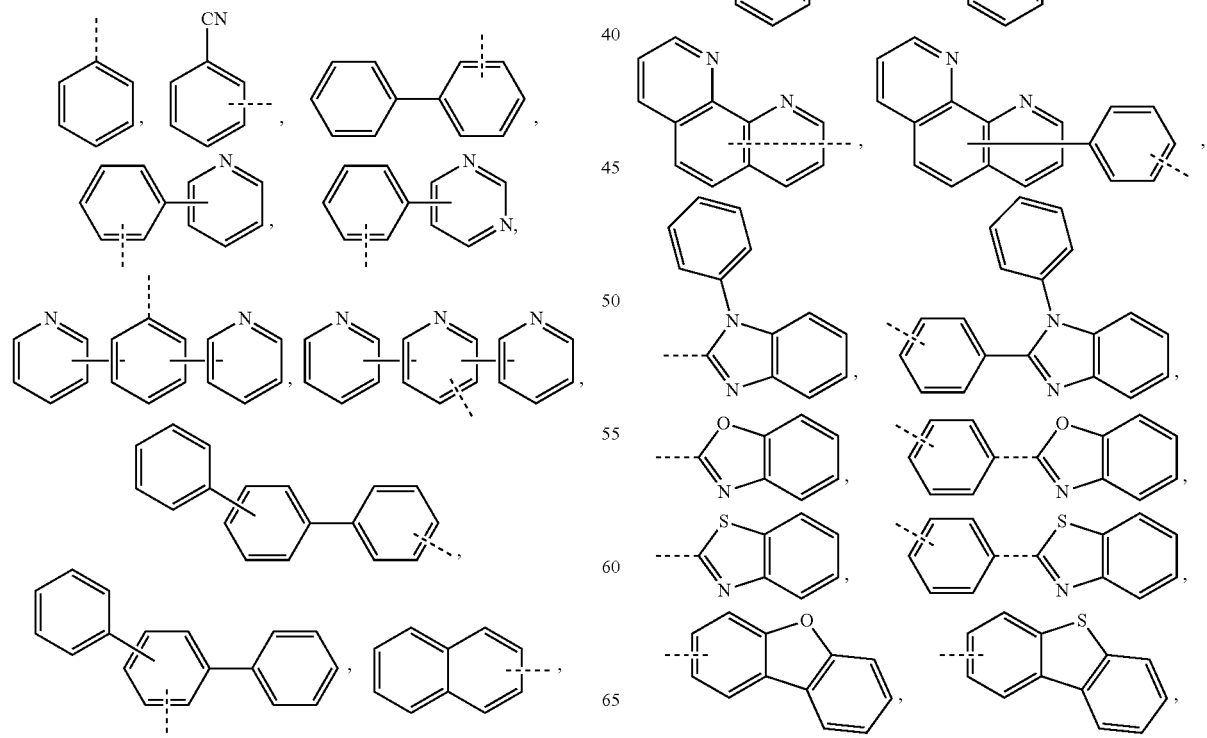

-continued

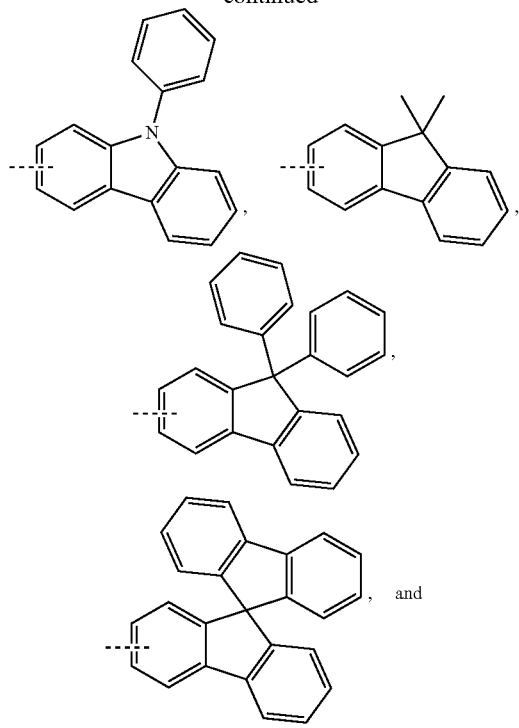

and the dashed line represents a linkage site of a group.

The substituted substituents are each independently selected from at least one of deuterium, cyano, halogen, unsubstituted or halogenated C1 to C10 (for example, C1, C2, C3, C4, C5, C6, C7, C8, C9 or C10) linear or branched alkyl, unsubstituted or halogenated C1 to C10 (for example, C1, C2, C3, C4, C5, C6, C7, C8, C9 or C10) alkoxy, C1 to C10 (for example, C1, C2, C3, C4, C5, C6, C7, C8, C9 or C10) alkylthio, C6 to C20 (for example, C6, C9, C10, C12, C14, C16, C18, etc.) aryl, C2 to C20 (for example, C3, C4, C5, C6, C8, C10, C12, C14, C16, C18, etc.) heteroaryl, or C6 to C18 (for example, C6, C9, C10, C12, C14, C16, C18, etc.) arylamino.

In an embodiment, $Ar_1$ and $Ar_2$ are each independently selected from any one of deuterium, halogen, cyano, phenyl or unsubstituted or halogenated C1 to C10 linear or branched alkyl.

The unsubstituted or halogenated C1 to C10 (for example, C1, C2, C3, C4, C5, C6, C7, C8, C9 or C10) linear or branched alkyl, for example, includes, but is not limited to, methyl, ethyl, n-propyl, isopropyl, n-butyl, isobutyl, tert-butyl, n-amyl, tert-amyl, isoamyl, neopentyl, n-hexyl, trifluoromethyl, perfluoroethyl, etc.

In a particular embodiment, the organic compound is selected from any one of the following compounds:

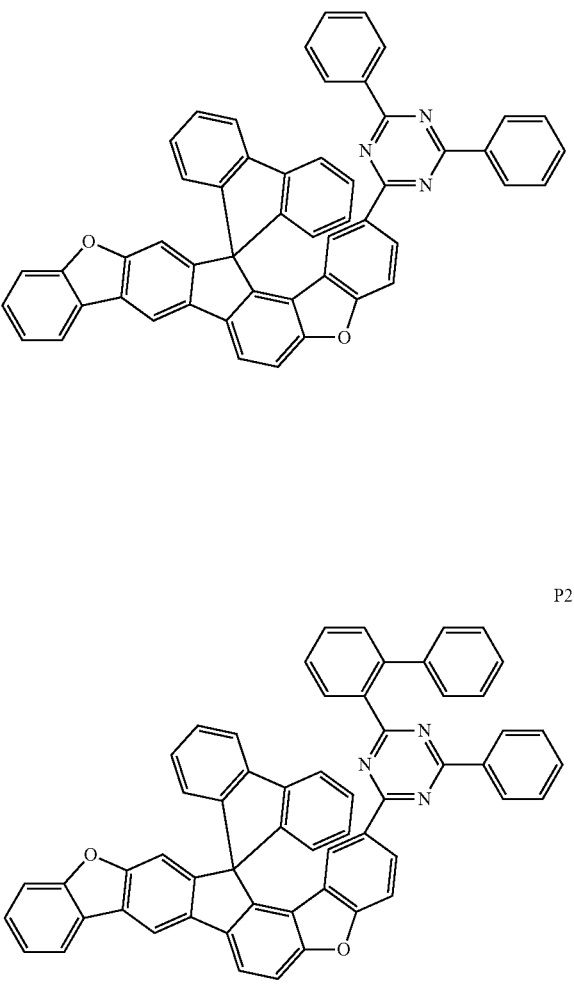

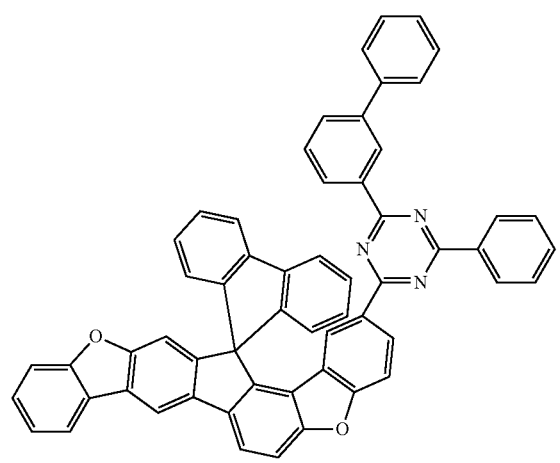

P4
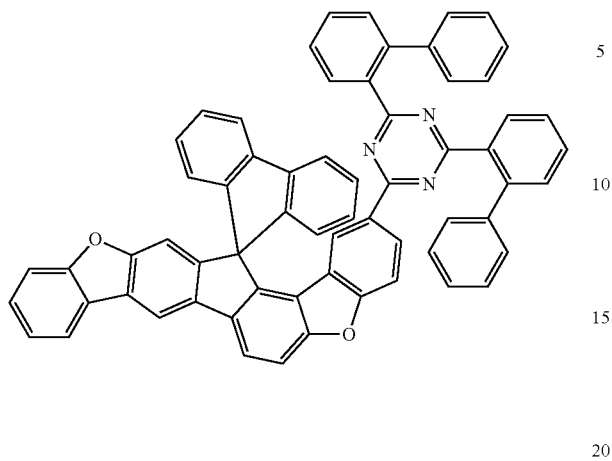
P5
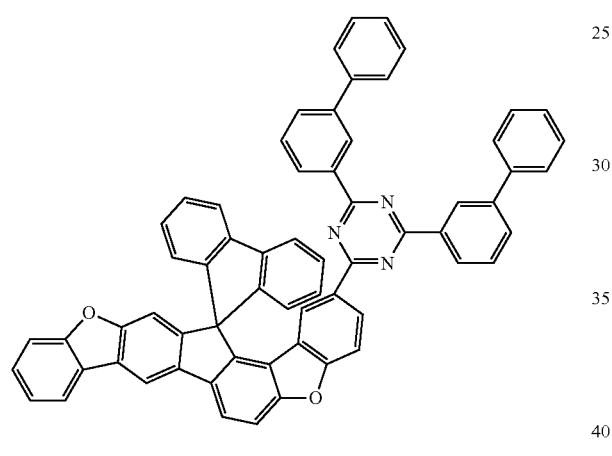
P6
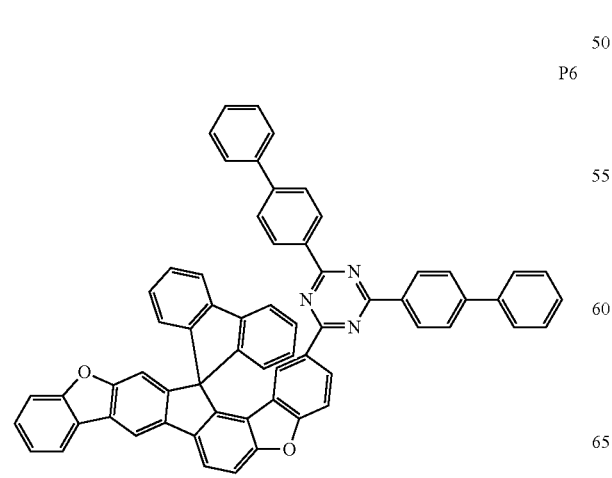
P7
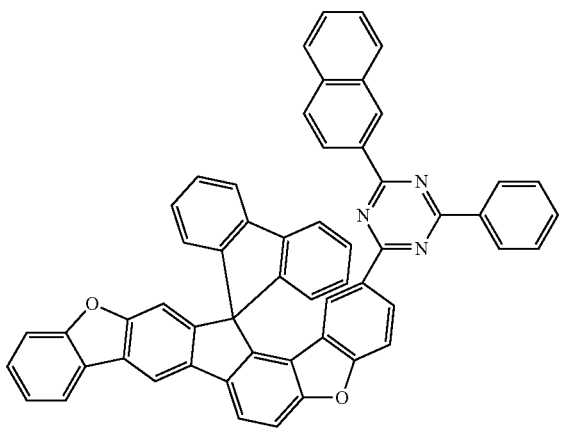
P8
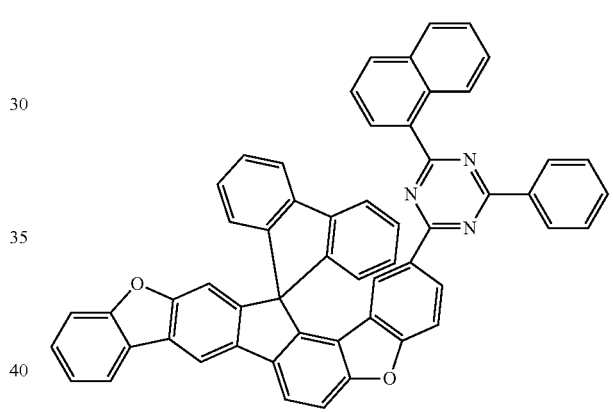
P9
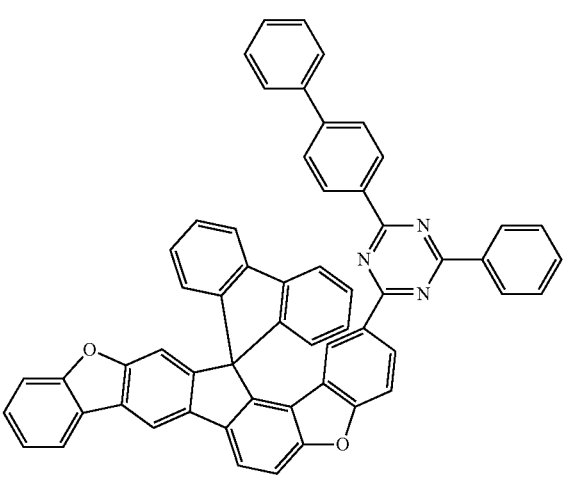

P10 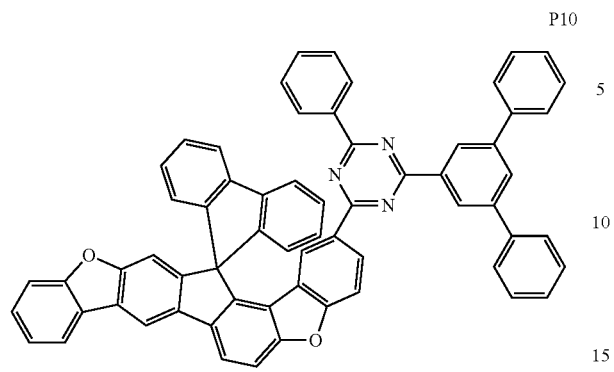
P11 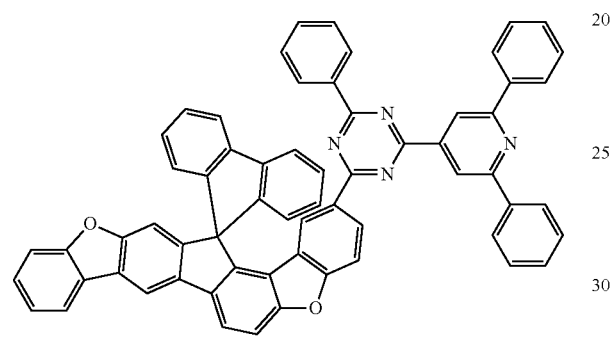
P12 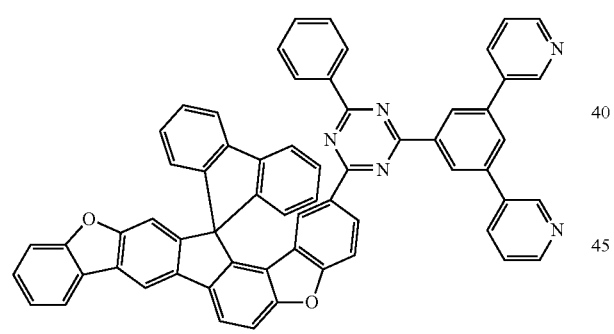
P13 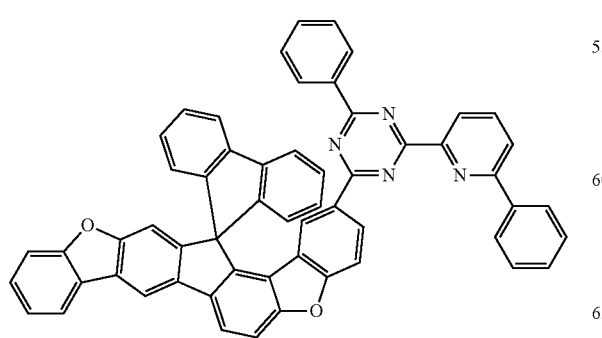
P14 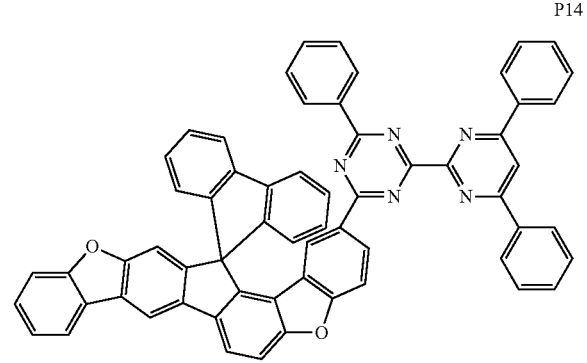
P15 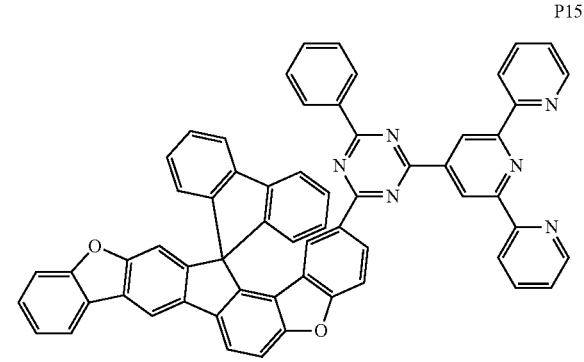
P16 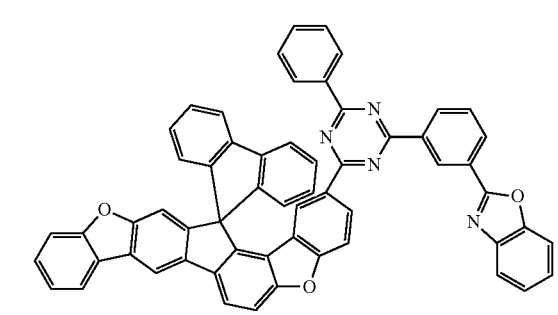
P17 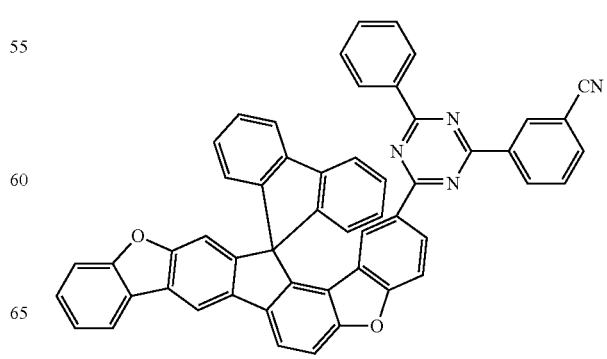

-continued
P18
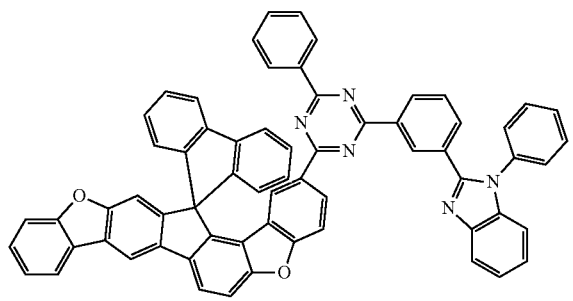
P19
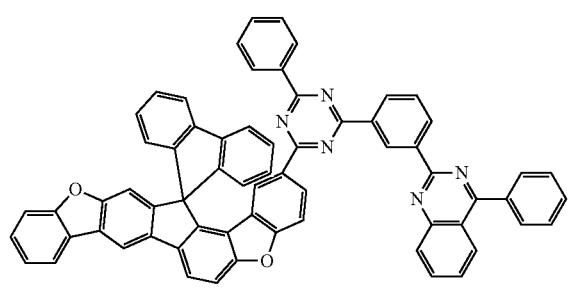
P20
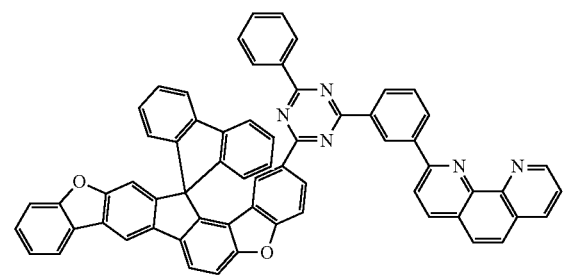
P21
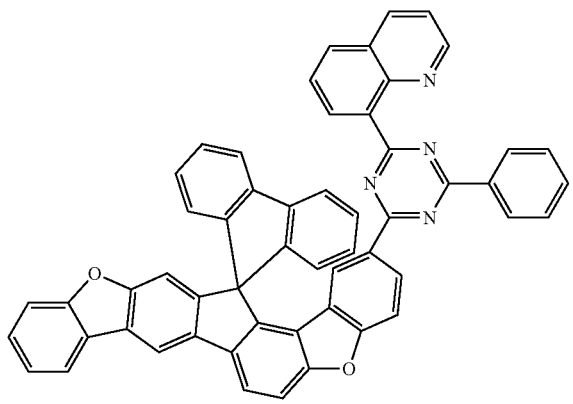
-continued
P22
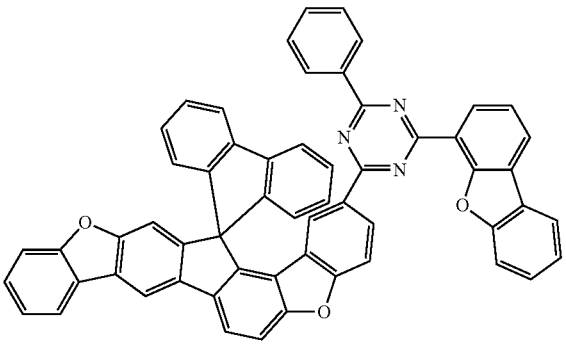
P23
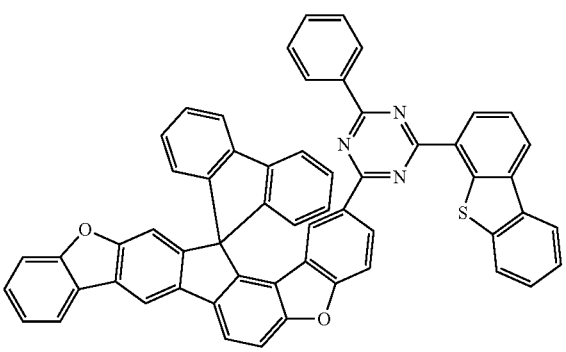
P24
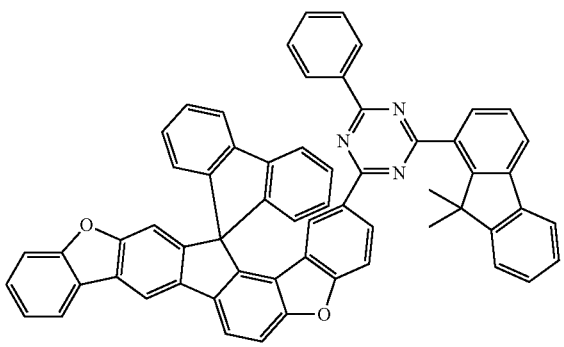
P25
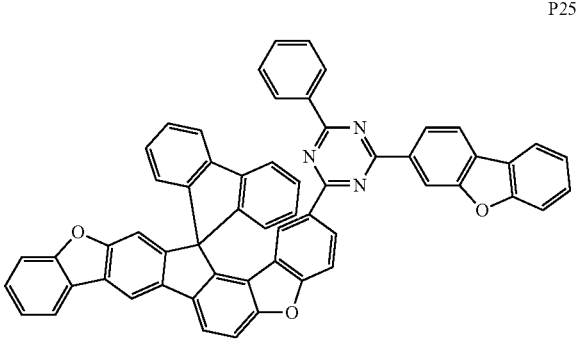

-continued
P26
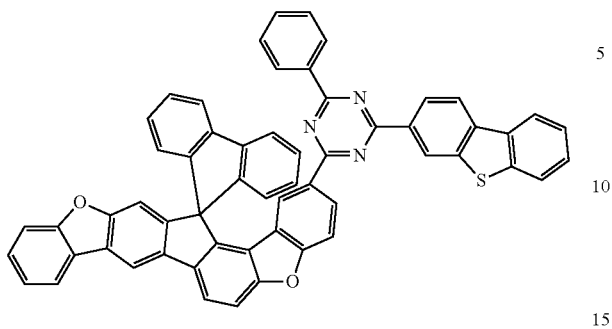
P27
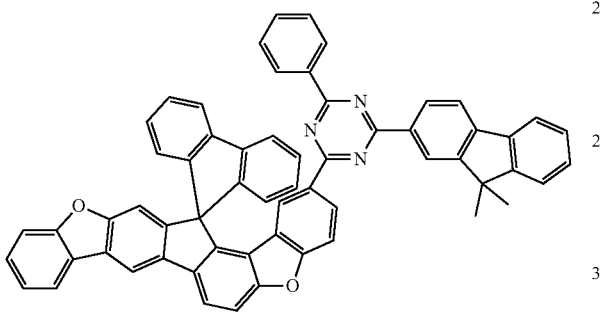
P28
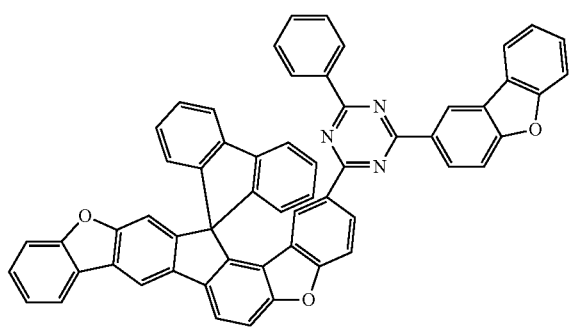
P29
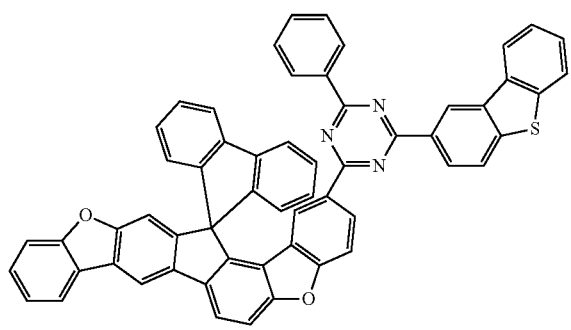
P30
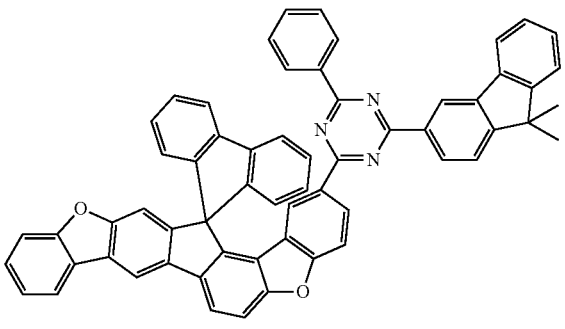
P31
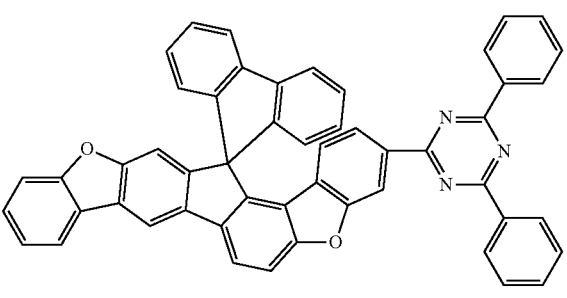
P32
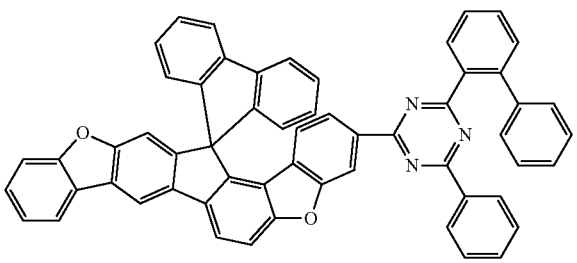
P33
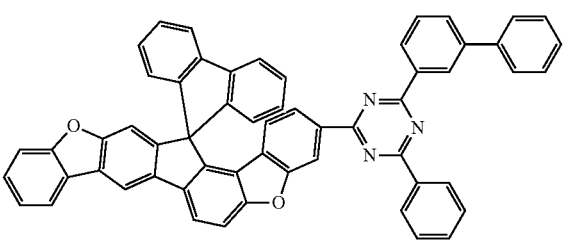
P34
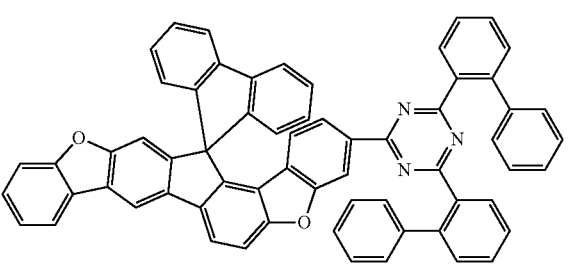

P35

P36

P37

P38

P39

P40

P41

P42

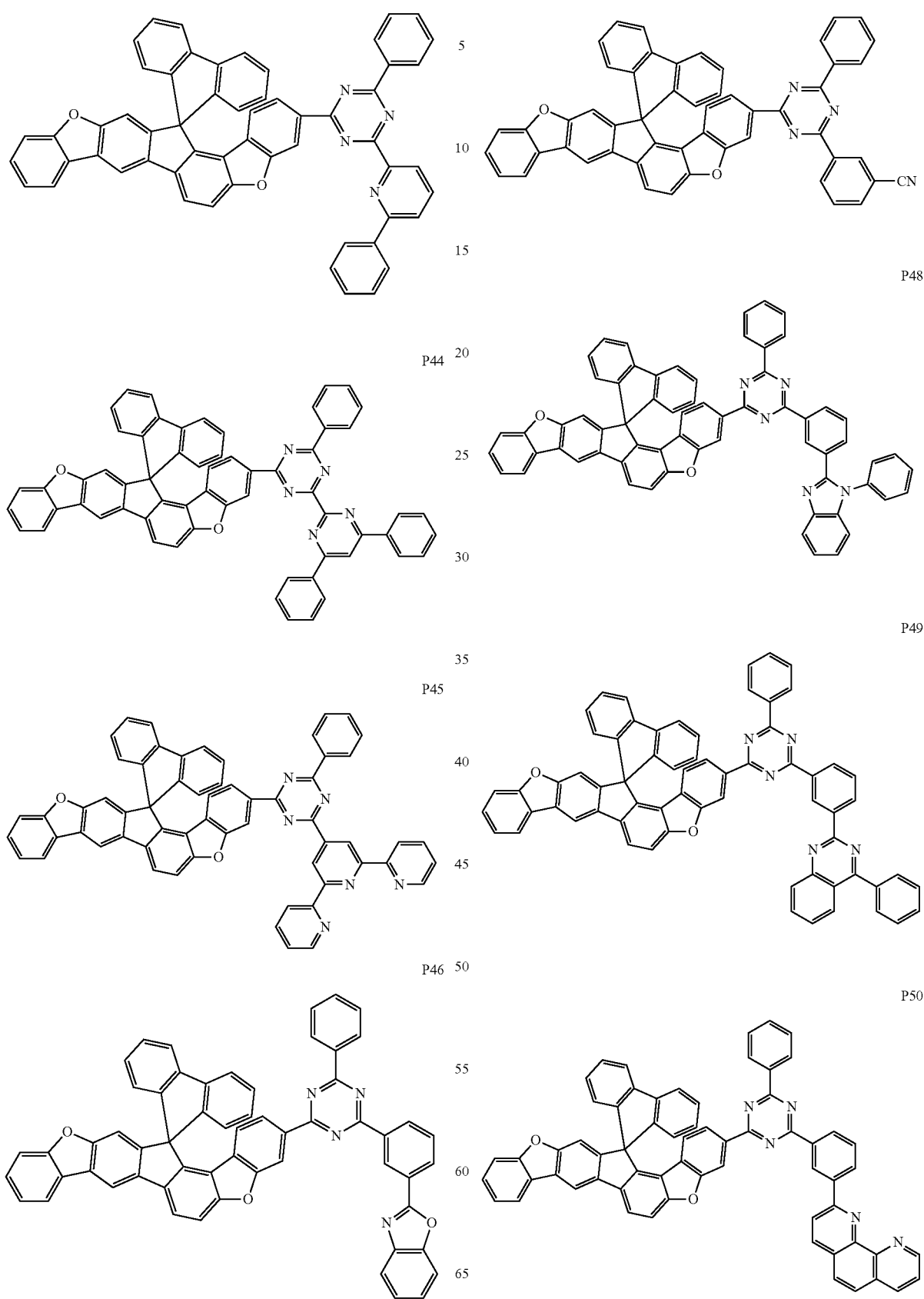

P51 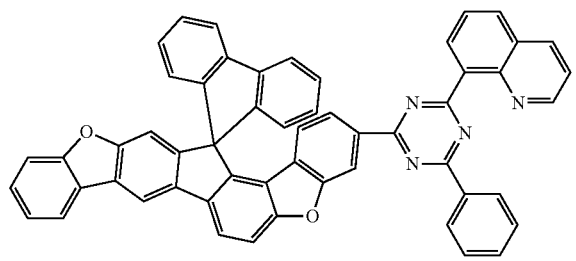
P52 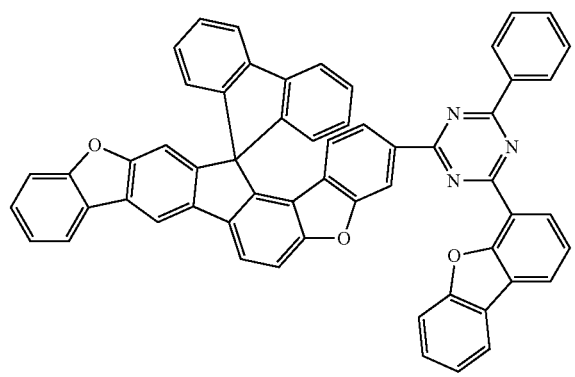
P55 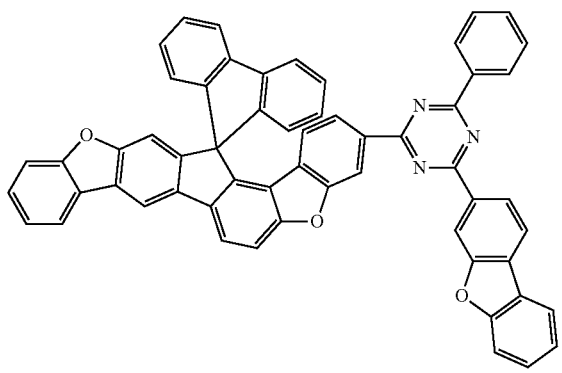
P56 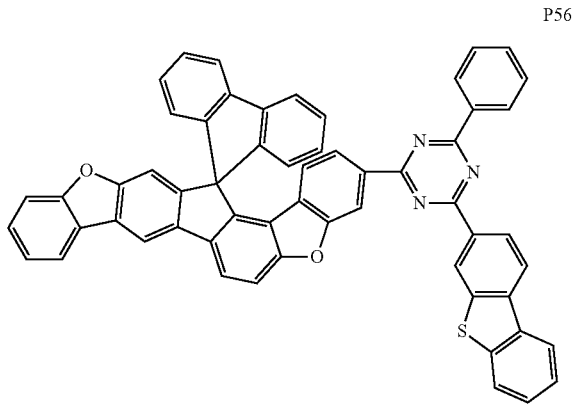
P53 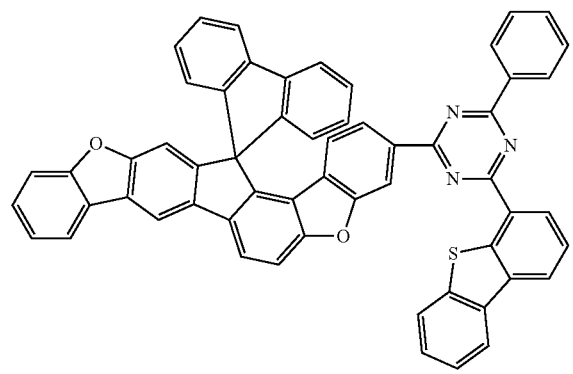
P57 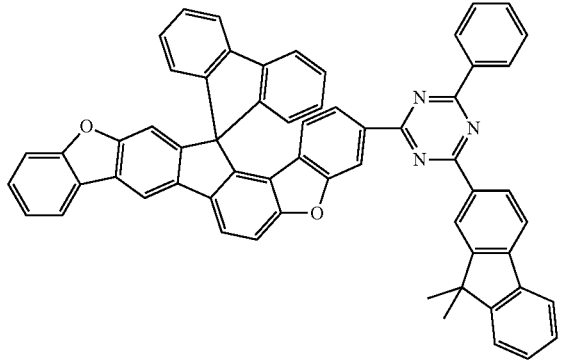
P54 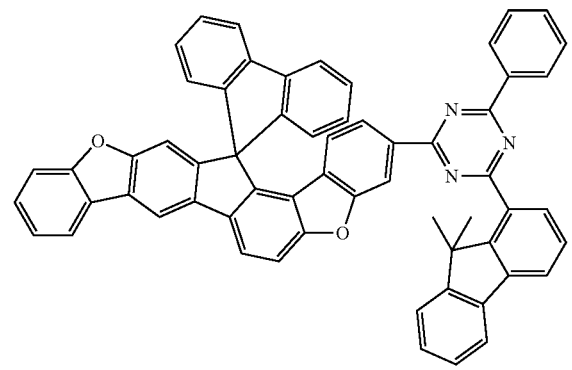
P58 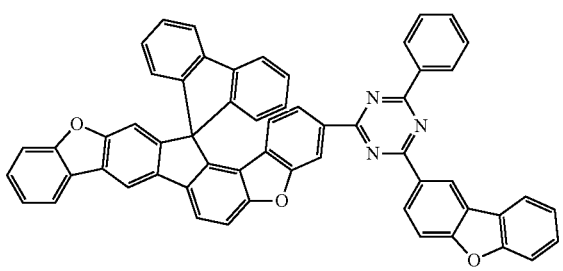

P59
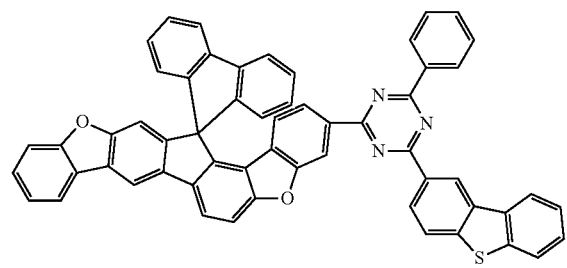
P60
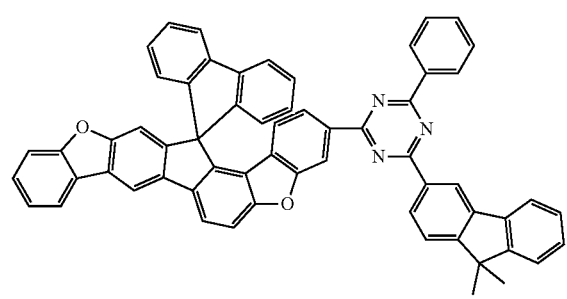
P61
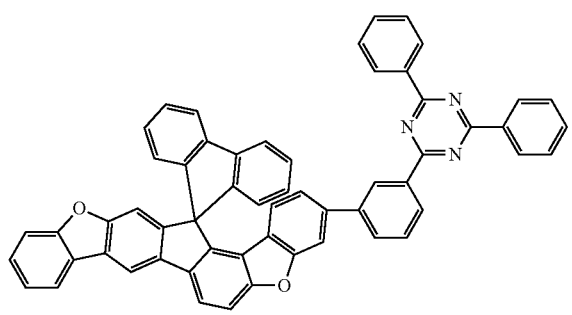
P62
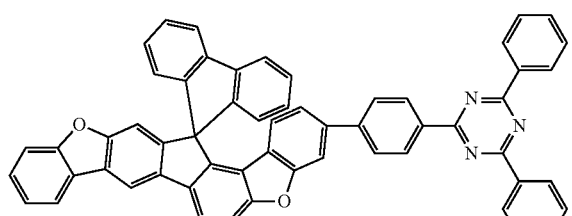
P63
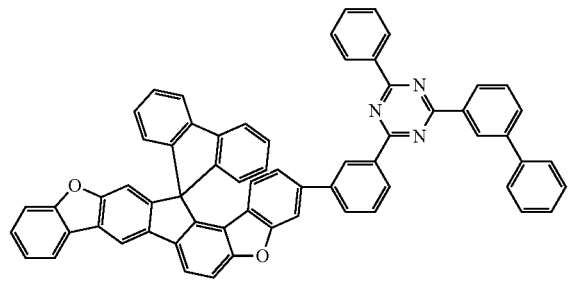
P64
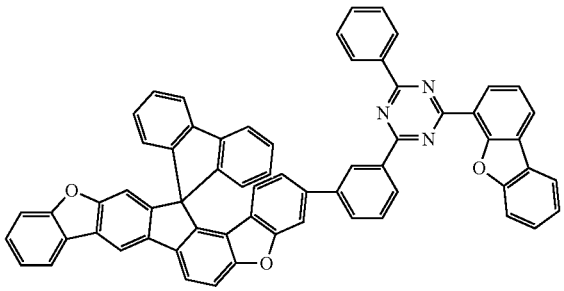
P65
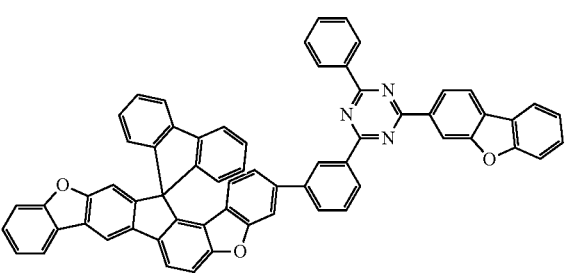
P66
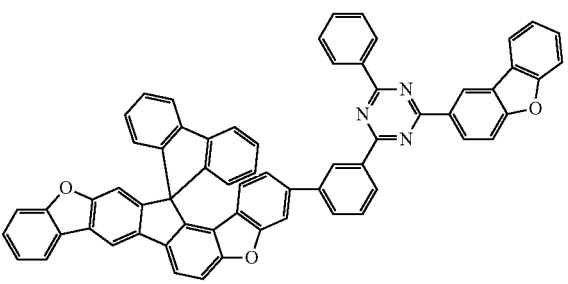
P67
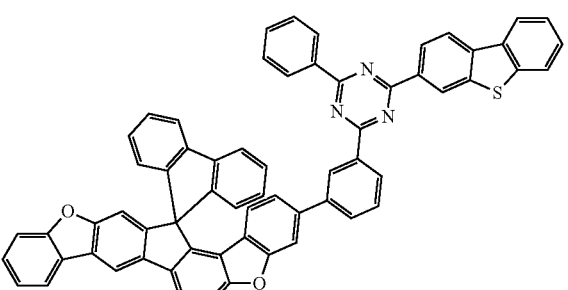
P68

P69
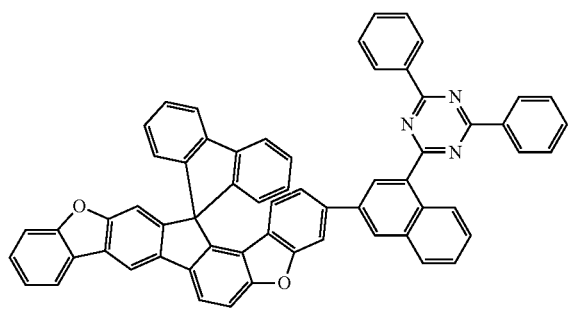
P70
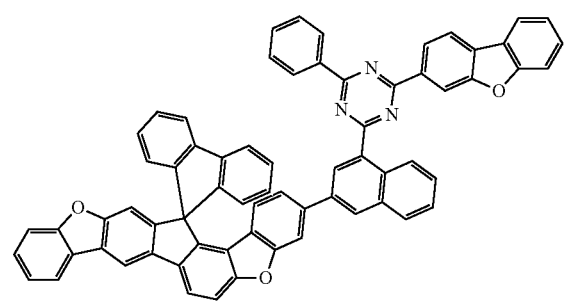
P71
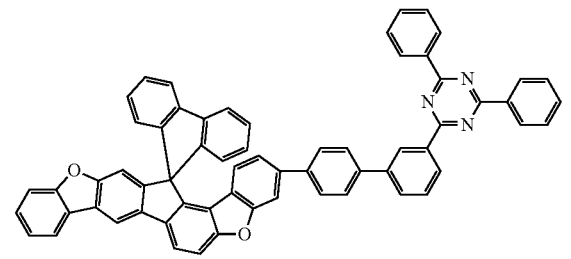
P72
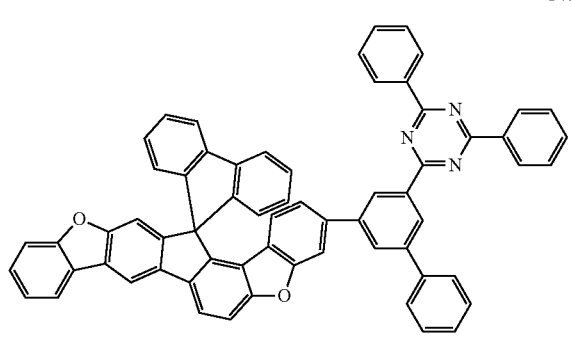
P73
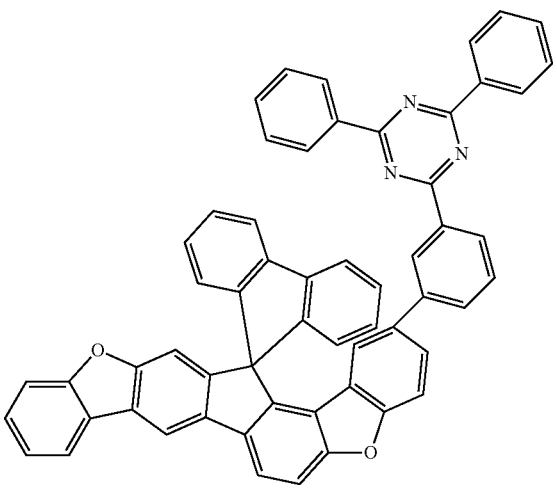
P74
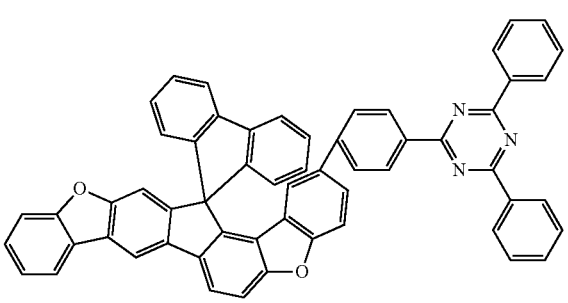
P75
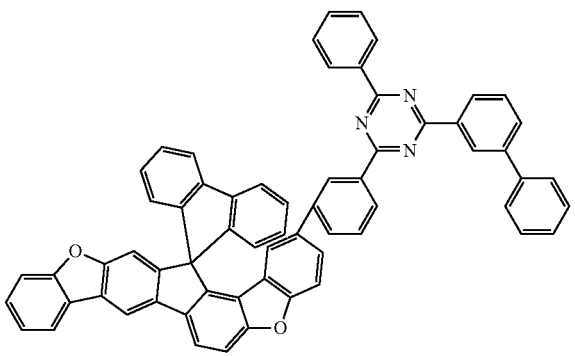
P76
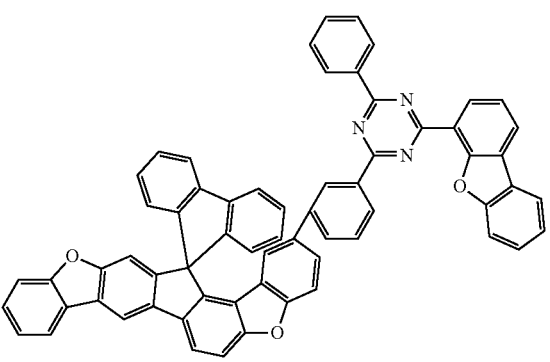

-continued
P77
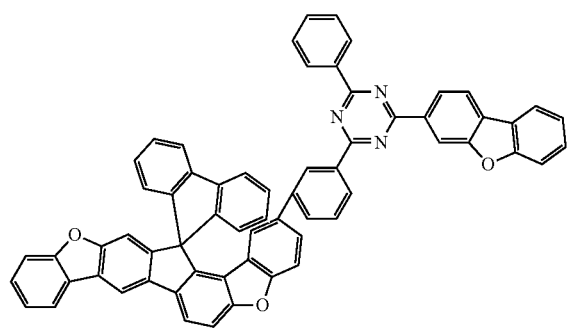
P78
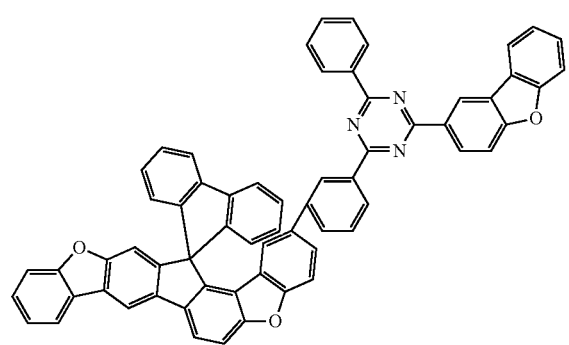
P79
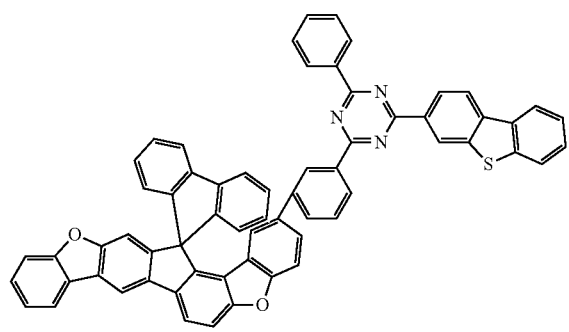
P80
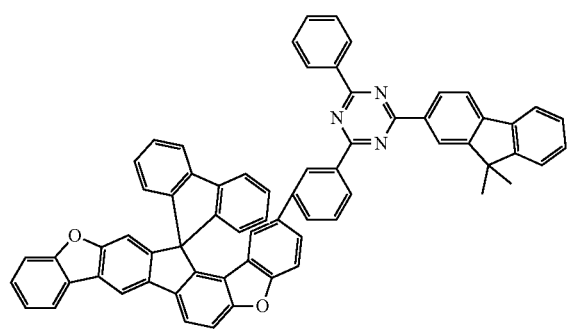
P81
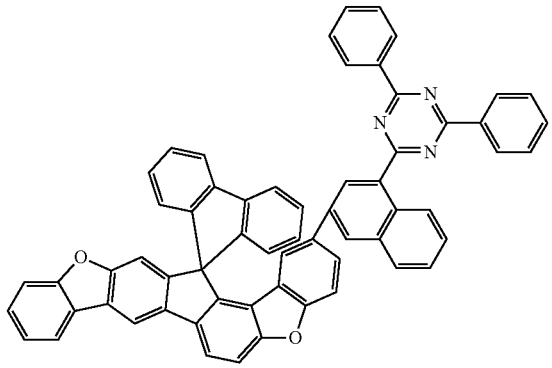
P82
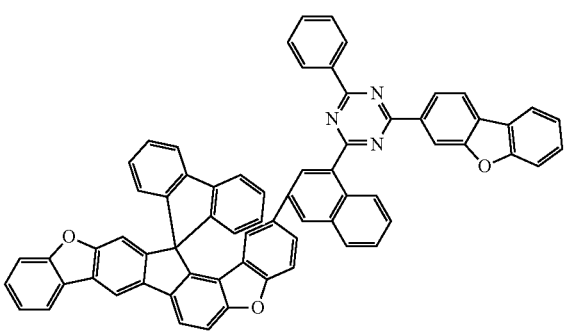
P83
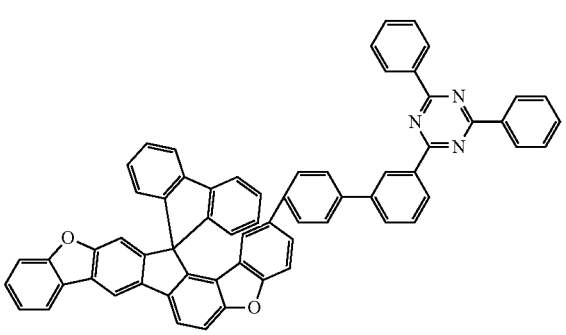
P84
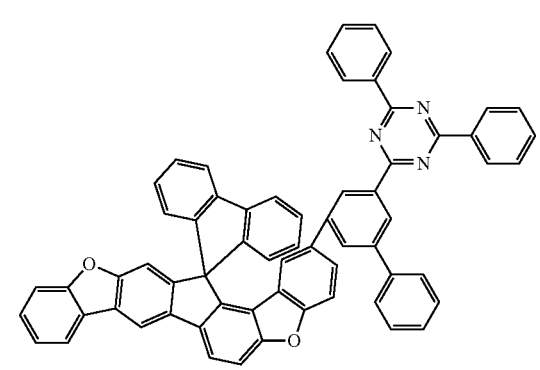

P85
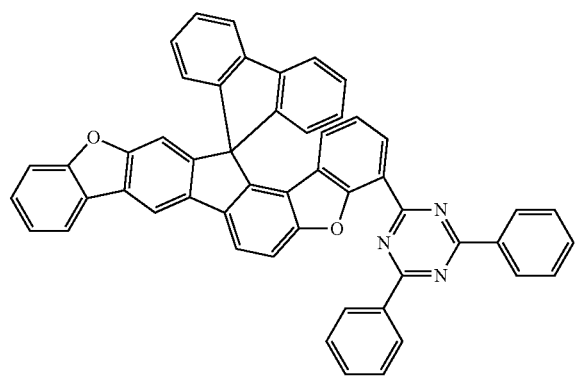
P86
P87
P88
P89
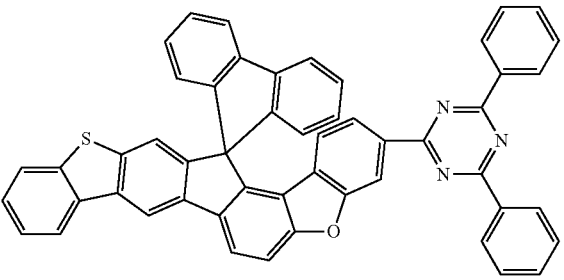
P90
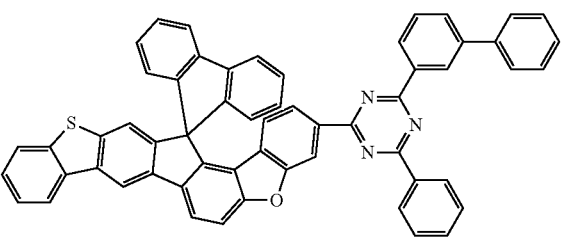
P91
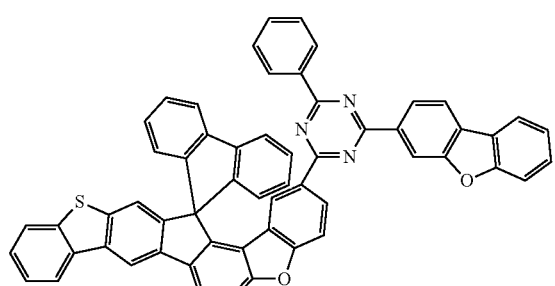
P92
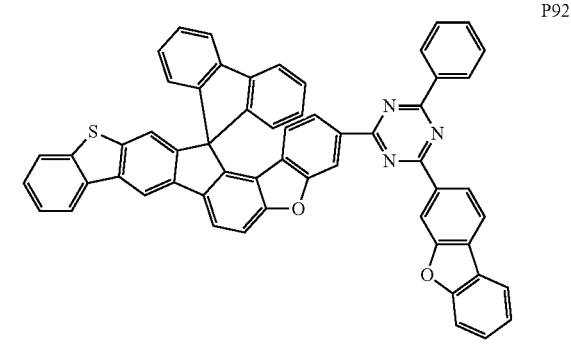
P93
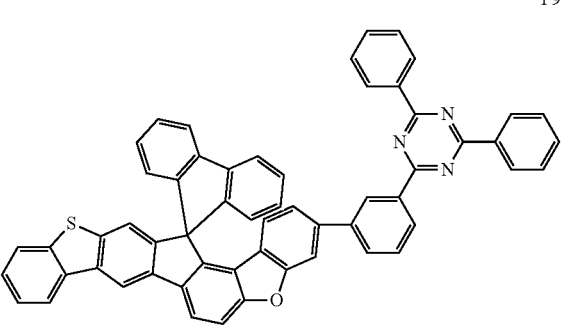

-continued
P94
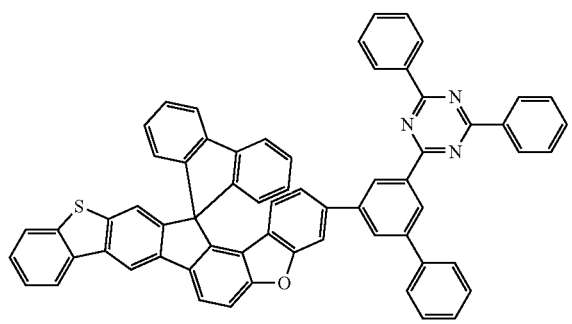
P95
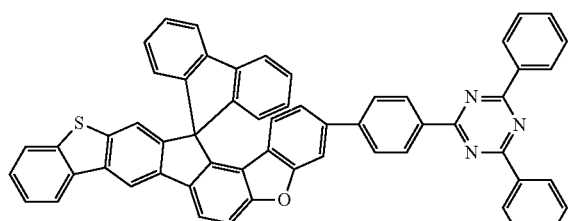
P96
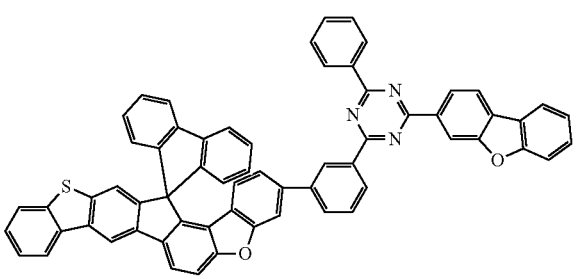
P97
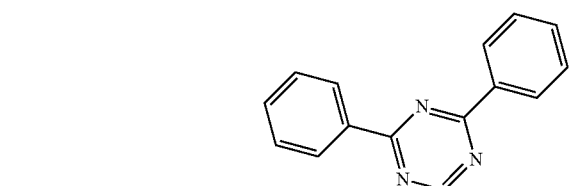
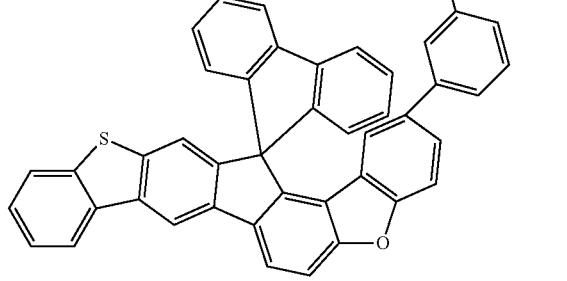
-continued
P98
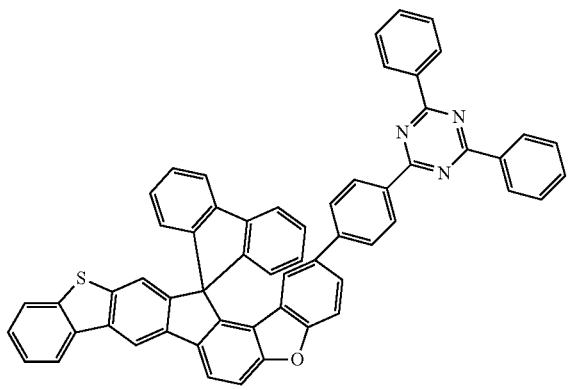
P99
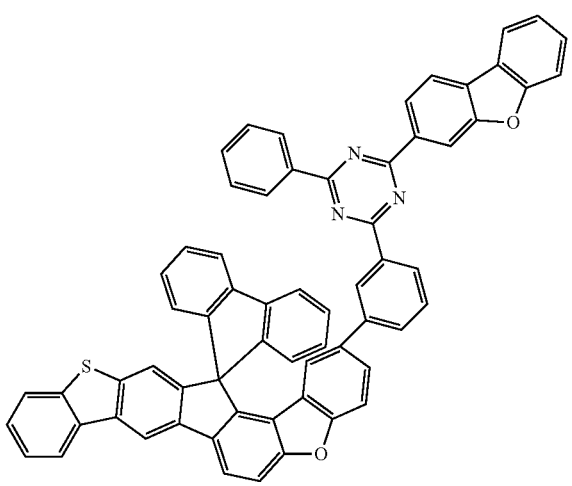
P100
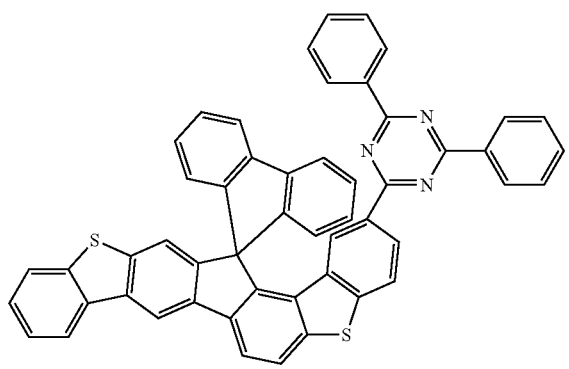
P101
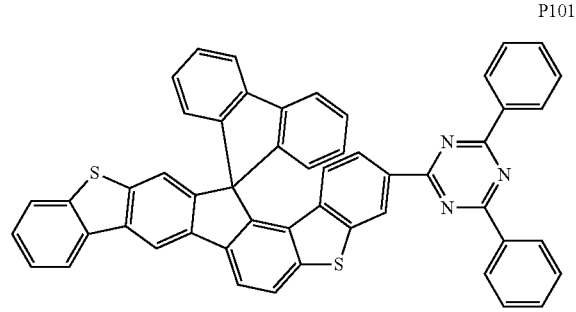

-continued
P102
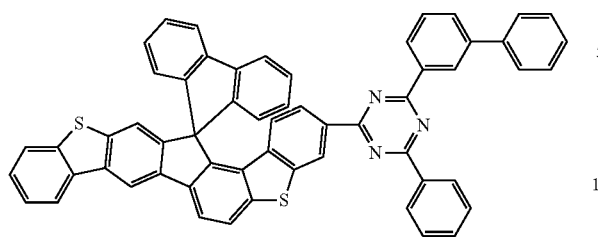
P103
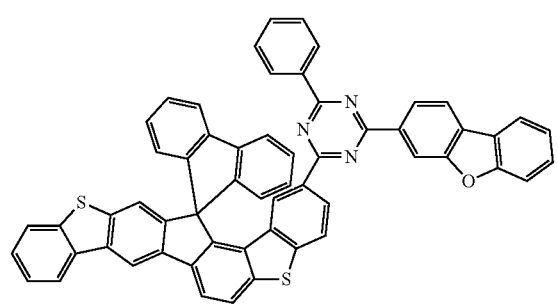
P104
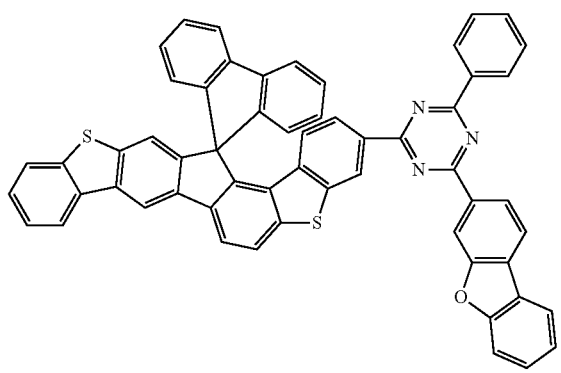
P105
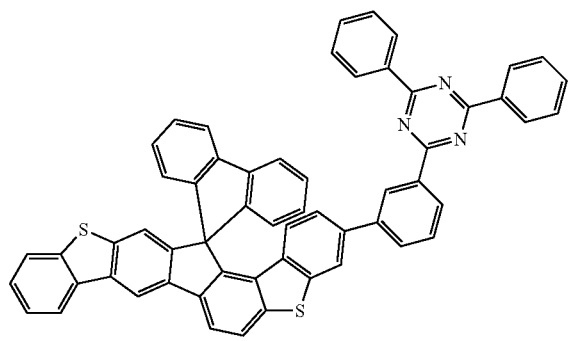
-continued
P106
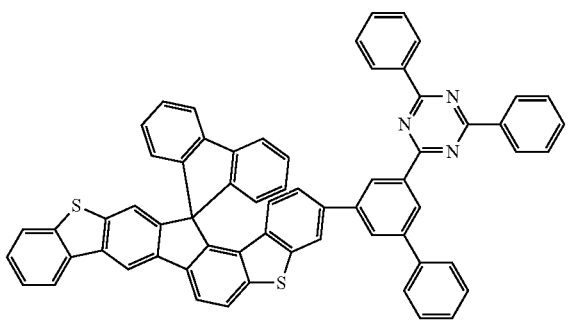
P107
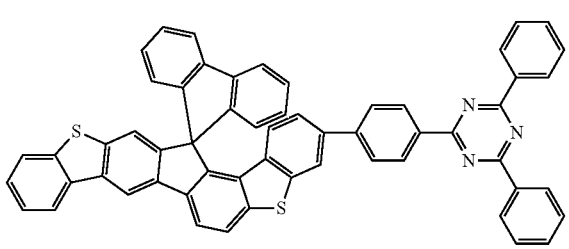
P108
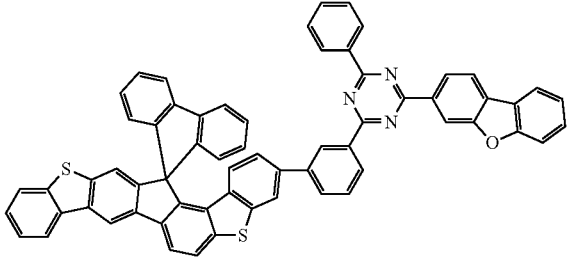
P109
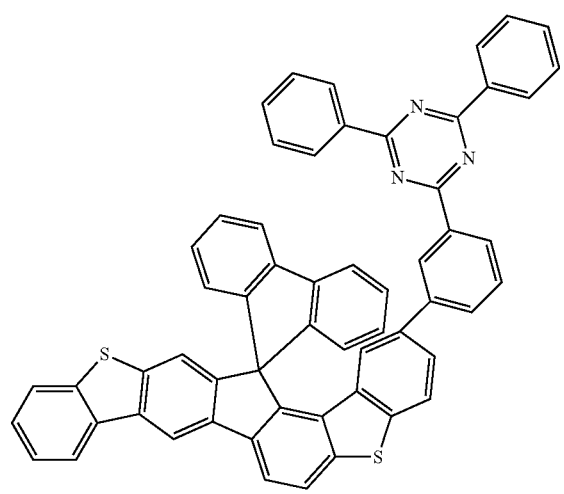

P110
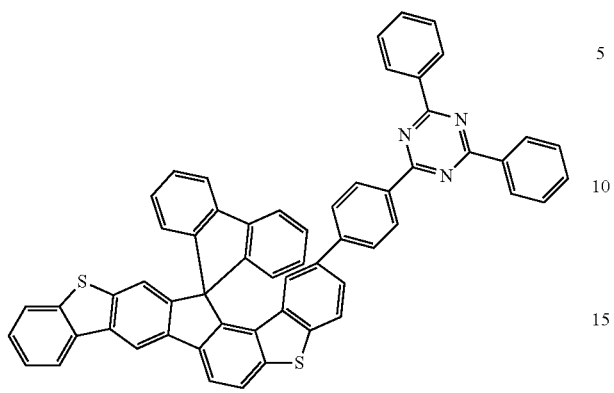
P114
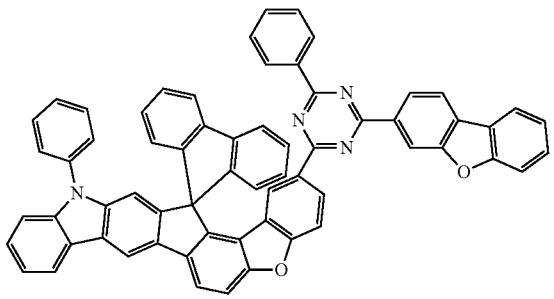
P111
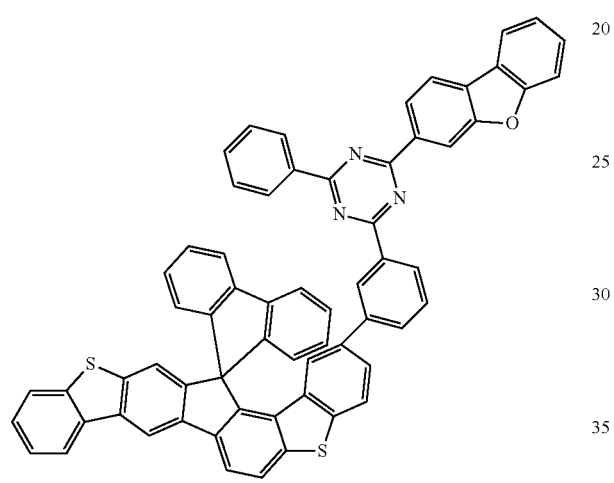
P115
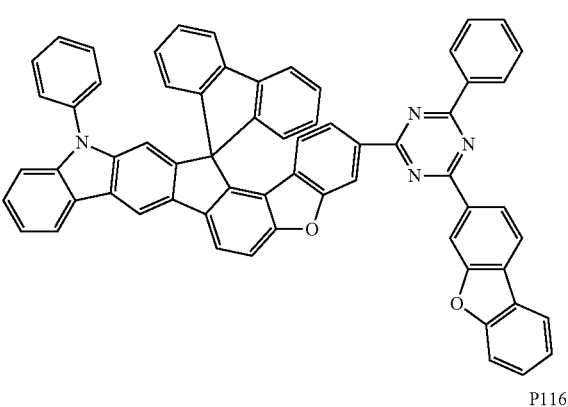
P112
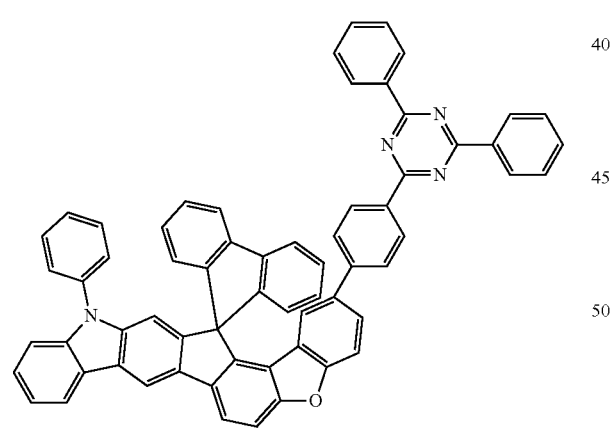
P116
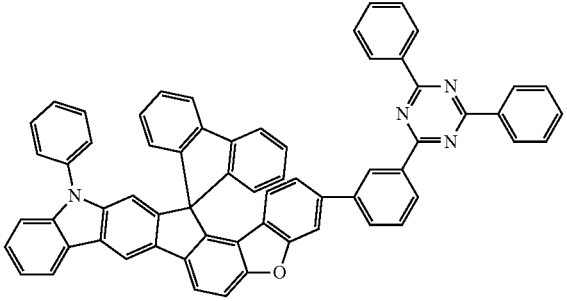
P113
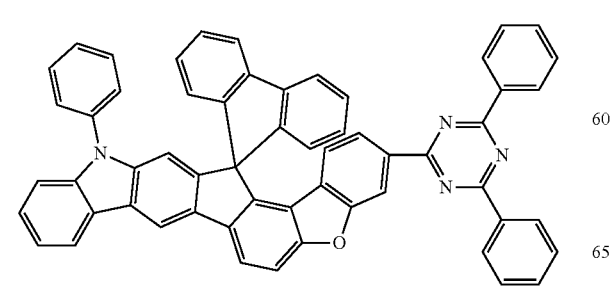
P117
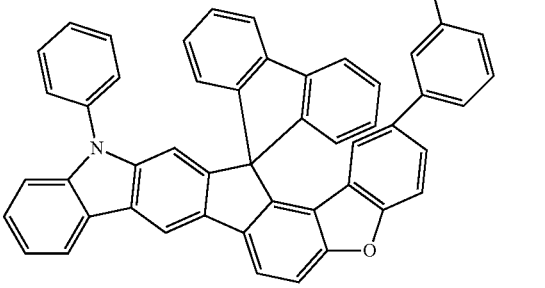

P118
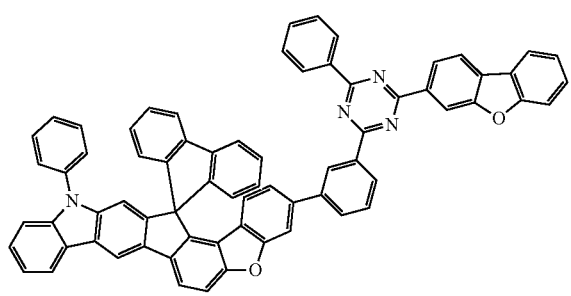
P119
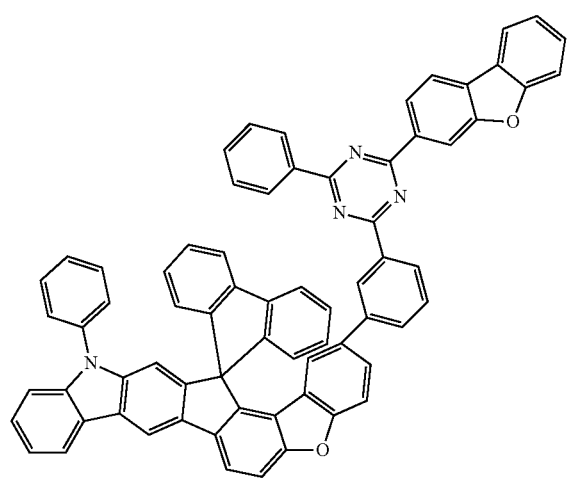
P120
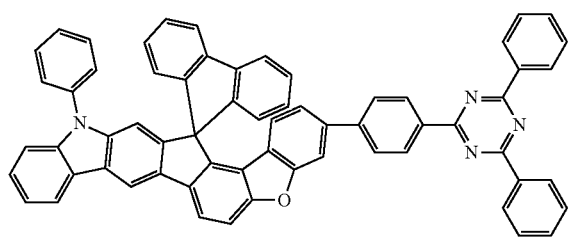
P121
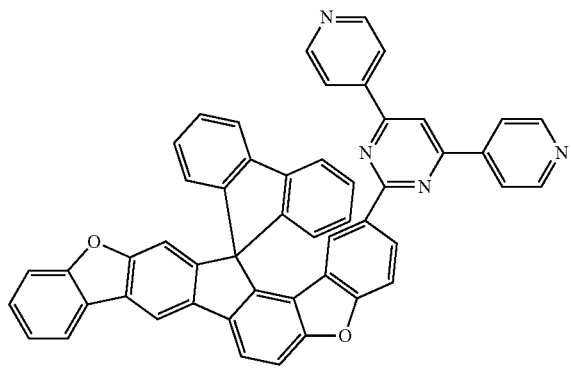
P122
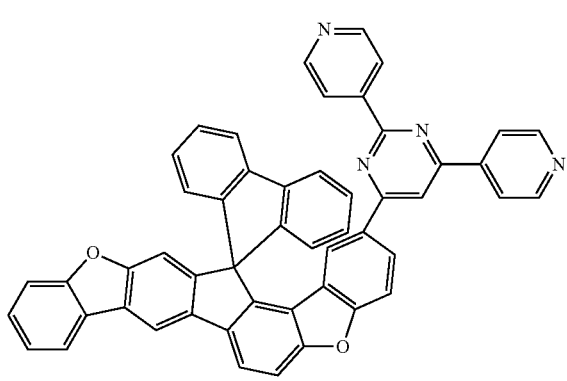
P123
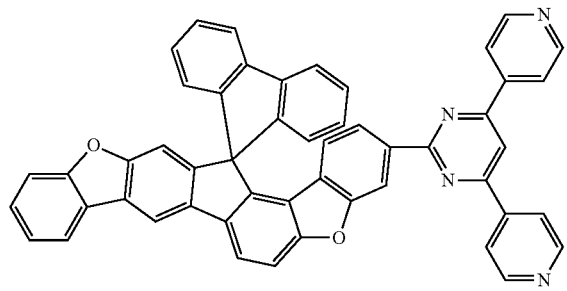
P124
P125
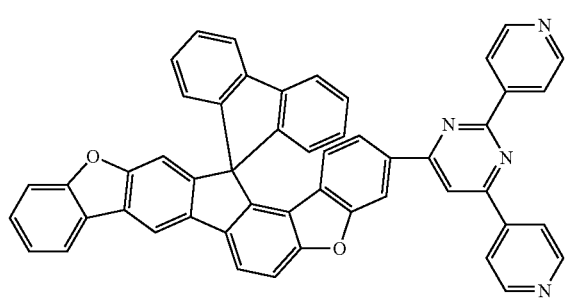

P126
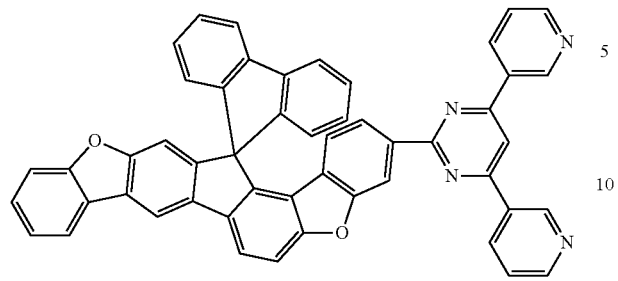
P127
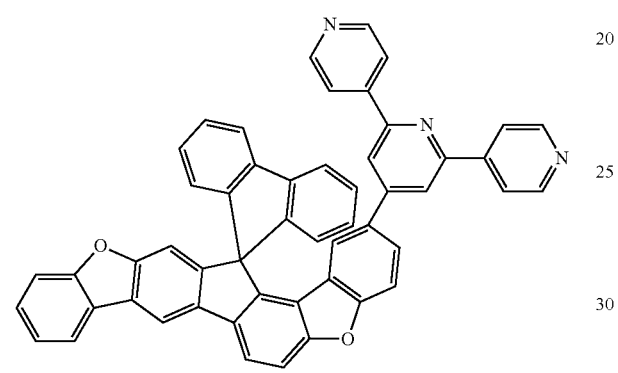
P128
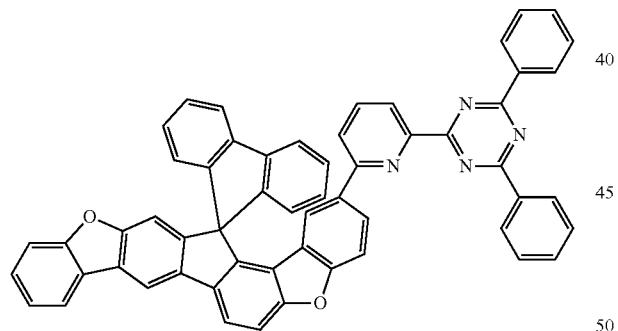
P129
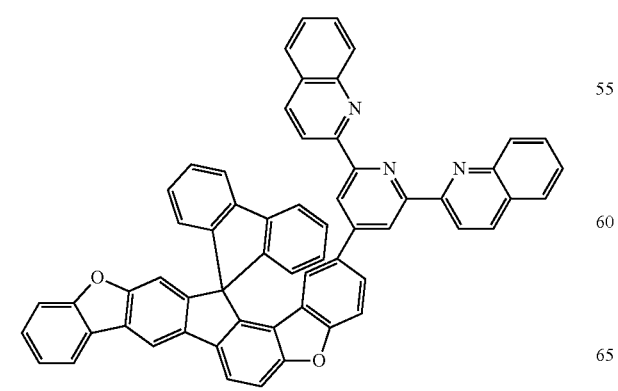
P130
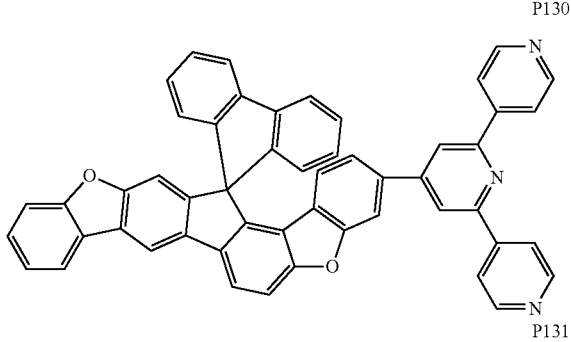
P131
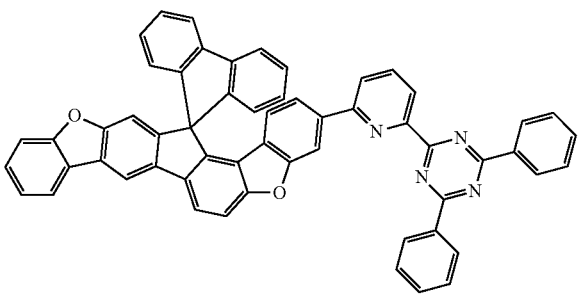
P132
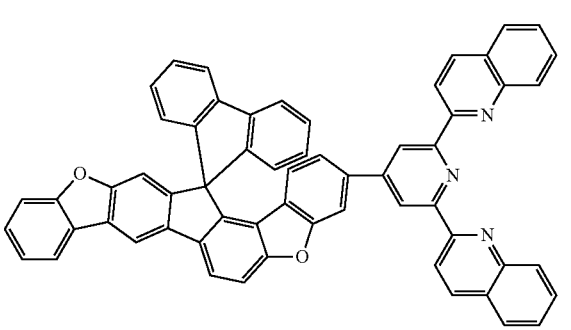
P133
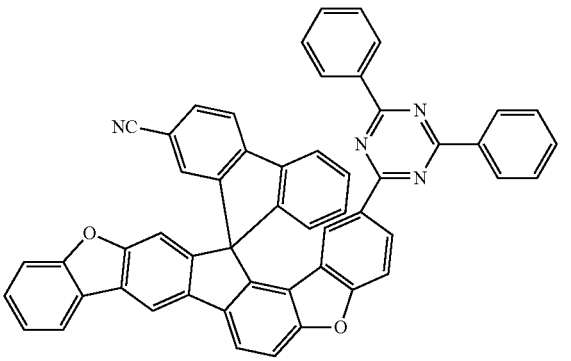
P134
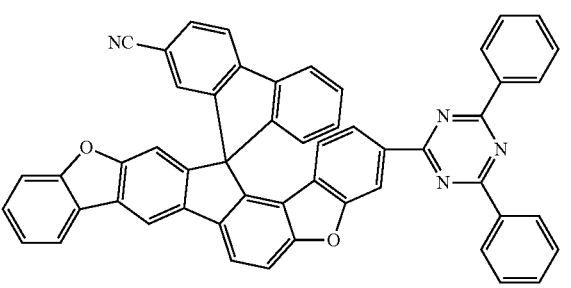

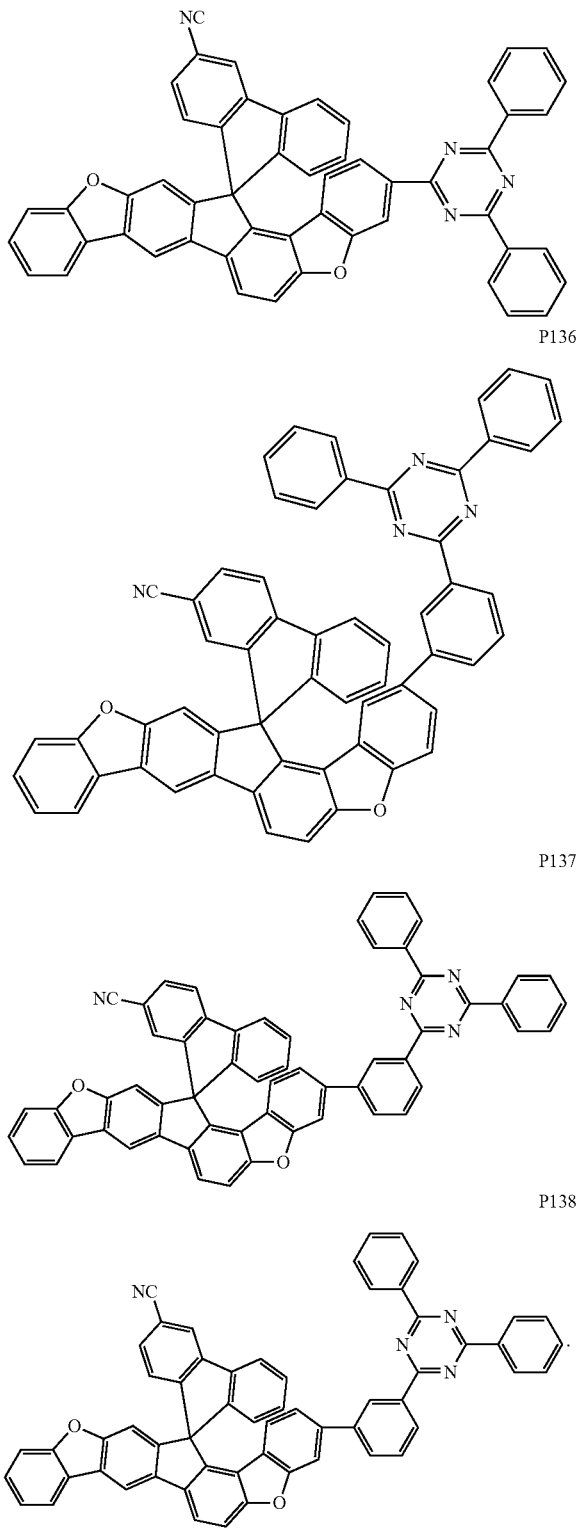

P135

P136

P137

P138

Embodiments of the present disclosure is to provide an electroluminescent material including the organic compound as described in the other embodiments.

One embodiment of the present disclosure is to provide an OLED device including an anode, a cathode, and an organic thin film layer located between the anode and the cathode, where the material of the organic thin film layer includes the electroluminescent material as described in other embodiments.

In an embodiment, the organic thin film layer includes an electron transport layer whose material includes the electroluminescent material as described in the other embodiments.

In an embodiment, the organic thin film layer includes a hole blocking layer whose material includes the electroluminescent material as described in the other embodiments.

In an embodiment, the organic thin film layer includes a light-emitting layer whose material includes the electroluminescent material as described in the other embodiments.

In an embodiment, the organic thin film layer further includes any one or a combination of at least two of a hole injection layer, a hole transport layer, an electron blocking layer or an electron injection layer.

In the OLED device provided by the present disclosure, the material of the anode may be a metal, a metal oxide or a conductive polymer, and the metal includes copper, gold, silver, iron, chromium, nickel, manganese, palladium, platinum, etc., as well as alloys thereof, the metal oxide includes indium tin oxide (ITO), indium zinc oxide (IZO), zinc oxide, indium gallium zinc oxide (IGZO), etc., and the conductive polymer includes polyaniline, polypyrrole, poly(3-methylthiophene), etc. In addition to the above-mentioned materials that are helpful for hole injection and combinations thereof, the material of the anode further includes known materials suitable to prepare the anode.

In the OLED device, the material of the cathode may be a metal or a multilayer metal material, and the metal includes aluminum, magnesium, silver, indium, tin, titanium, etc., as well as alloys thereof, and the multilayer metal material includes LiF/Al, LiO$_2$/Al, BaF$_2$/Al, etc. In addition to the above-mentioned materials that are helpful for electron injection and combinations thereof, the material of the cathode further includes known materials suitable to prepare the cathode.

In the OLED device, the organic thin film layer includes at least one light-emitting layer (EML) and any one or a combination of at least two of a hole injection layer (HIL), a hole transport layer (HTL), an electron blocking layer (EBL), a hole blocking layer (HBL), an electron transport layer (ETL) or an electron injection layer (EIL) that are disposed on two sides of the light-emitting layer. In addition to the organic compound as described in one embodiment of the present disclosure, the hole/electron injection and transport layers may also include a carbazole compound, an aromatic amine compound, a benzimidazole compound, a metal compound, etc. The OLED device may further be provided with a capping layer (CPL) disposed on the cathode (a side of the cathode away from the anode).

As shown in the FIGURE which is a schematic diagram of an OLED device, the OLED device includes an anode 101, a cathode 102, and a light-emitting layer 103 disposed between the anode 101 and the cathode 102, where a first organic thin film layer 104 and a second organic thin film layer 105 are disposed on two sides of the light-emitting layer 103 respectively. The first organic thin film layer 104 is any one, or a combination of, at least two of a hole injection layer (HIL), a hole transport layer (HTL) or an electron blocking layer (EBL), and the second organic thin film layer 105 includes any one or a combination of at least two of a hole blocking layer (HBL), an electron transport layer (ETL) or an electron injection layer (EIL). The cathode 102 (a side of the cathode 102 away from 105) may further be provided with a capping layer (CPL).

The OLED device may be prepared by the following method: forming an anode on a transparent or opaque smooth substrate, forming an organic thin film layer on the anode, and forming a cathode on the organic thin film layer. The organic thin film layer may be formed by using known film-forming methods such as evaporation, sputtering, spin coating, dipping, ion plating, etc.

Another embodiment of the present disclosure is to provide a display device including the OLED device as described in the other embodiments.

In the present disclosure, the organic compound having the structure as shown in Formula I may be prepared according to the following synthesis route:

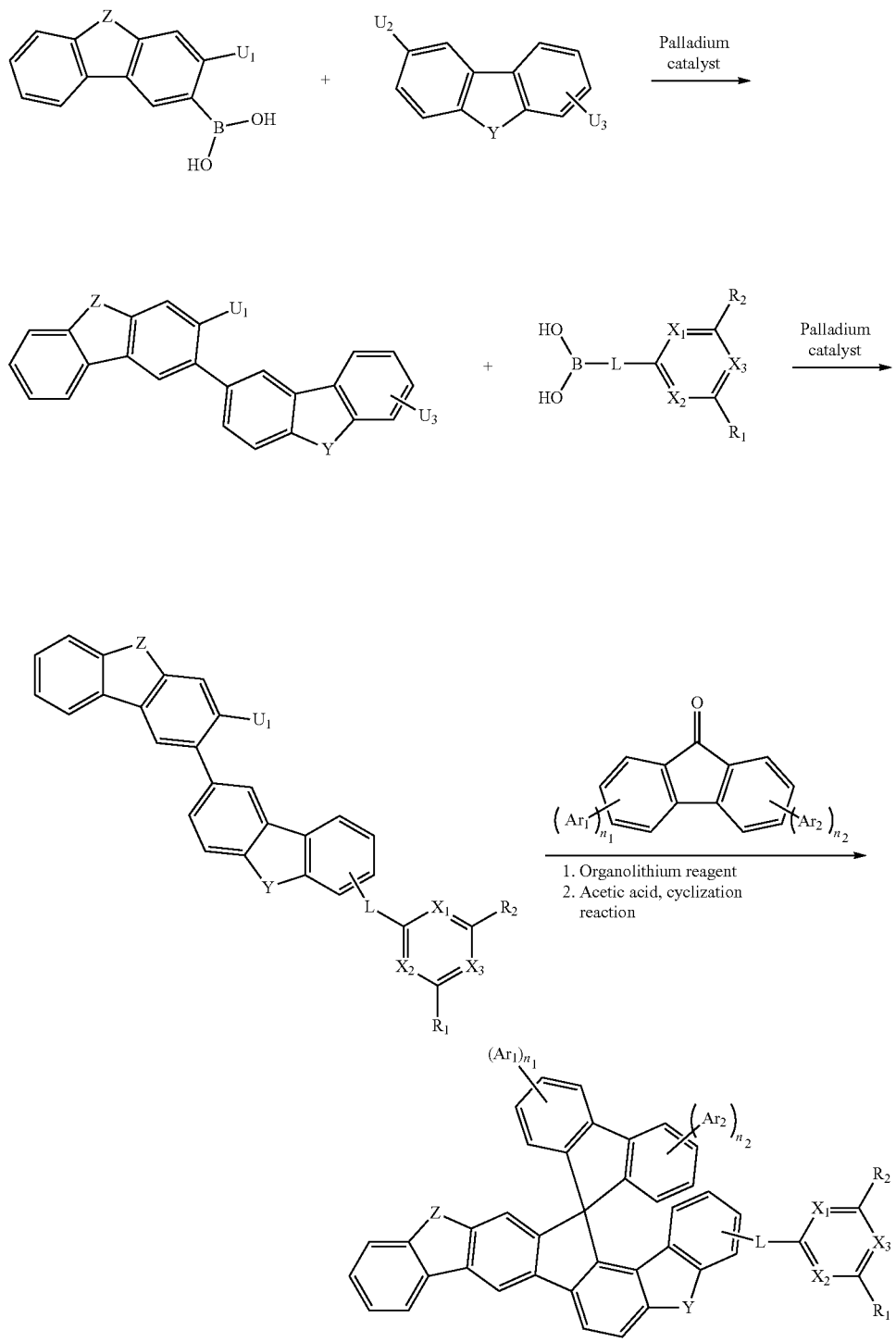

In the above synthesis route, $X_1$, $X_2$, $X_3$, Y, Z, L, $R_1$, $R_2$, $Ar_1$, $Ar_2$, $n_1$, and $n_2$ have the same ranges as defined in Formula I, and $U_1$, $U_2$, and $U_3$ are each independently selected from halogen (for example, chlorine, bromine, or iodine).

Preparation examples of the organic compound of the present disclosure are described below for purposes of example.

Example 1

An organic compound P1 is provided, and the structure of the organic compound P1 is as follows:

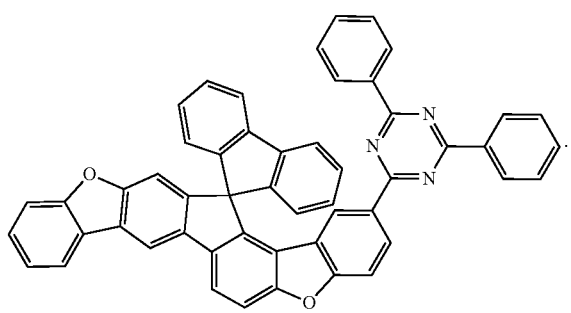

P1

The preparation method includes the steps described below.

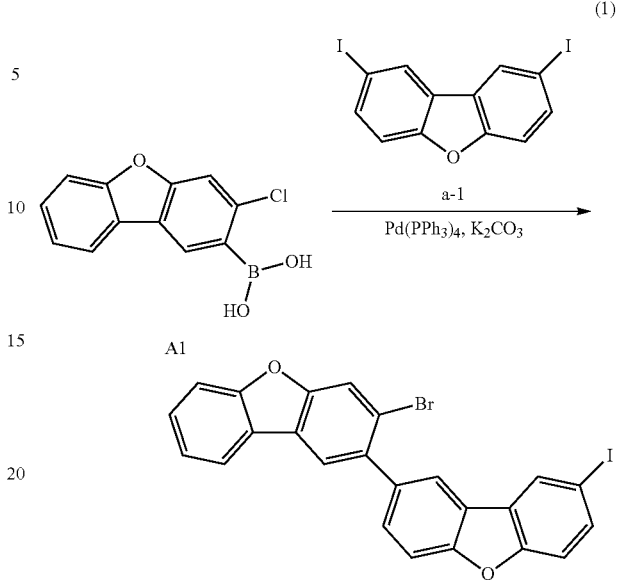

(1)

Under nitrogen atmosphere, a reaction solvent consisting of toluene, ethanol and water in the ratio of 7:2:1 was added to a reaction flask, then $K_2CO_3$ (10 mmol, aq), intermediate reactant A1 (5 mmol), reactant a-1 (5 mmol), and tetrakis(triphenylphosphine)palladium $Pd(PPh_3)_4$ (0.25 mmol) were added in sequence, and the mixture was heated to 80° C. and reacted overnight. After the reaction was complete, the reaction solution was cooled to room temperature, dichloromethane/$H_2O$ were added for extraction, and the collected organic phases were dried with anhydrous $Na_2SO_4$. The filtrate was collected by suction filtration, the solvent was removed through rotary evaporation, and the residue was purified by column chromatography to give intermediate B1 (with a yield of 72%).

MALDI-TOF-MS (m/z) obtained by matrix-assisted laser desorption/ionization time-of-flight mass spectrometry: $C_{24}H_{12}BrIO_2$, calculated value: 537.91, measured value: 538.20.

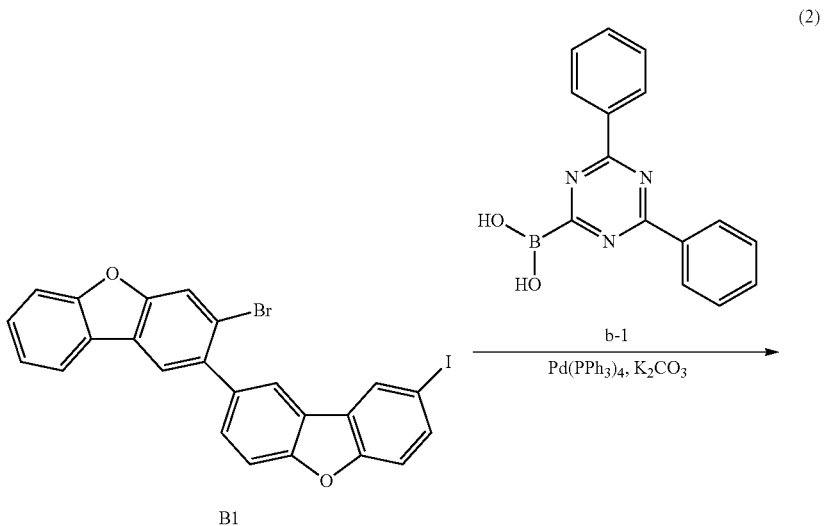

(2)

-continued

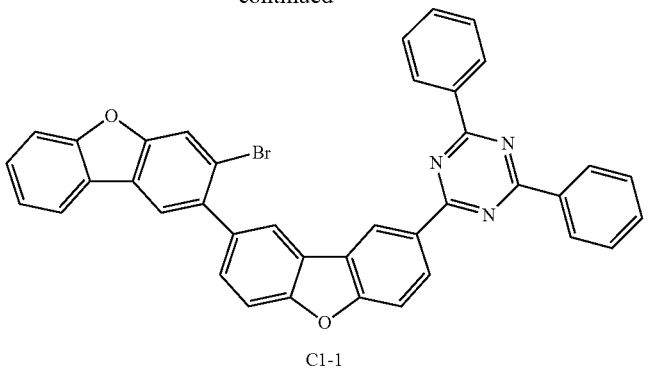

C1-1

Under nitrogen atmosphere, a reaction solvent consisting of toluene, ethanol and water in the ratio of 7:2:1 was added to a reaction flask, then $K_2CO_3$ (8 mmol, aq), intermediate reactant B1 (4 mmol), reactant b-1 (4 mmol), and $Pd(PPh_3)_4$ (0.2 mmol) were added in sequence, and the mixture was heated to 80° C. and reacted overnight. After the reaction was complete, the reaction solution was cooled to room temperature, dichloromethane/$H_2O$ were added for extraction, and the collected organic phases were dried with anhydrous $Na_2SO_4$. The filtrate was collected by suction filtration, the solvent was removed through rotary evaporation, and the residue was purified by column chromatography to give intermediate C1-1 (with a yield of 75%).

MALDI-TOF MS (m/z): $C_{39}H_{22}BrN_3O_2$, calculated value: 643.09, measured value: 643.30.

(3)

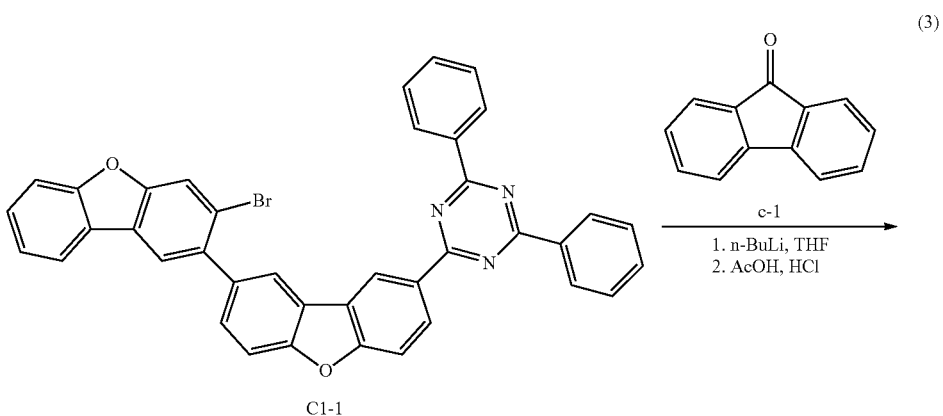

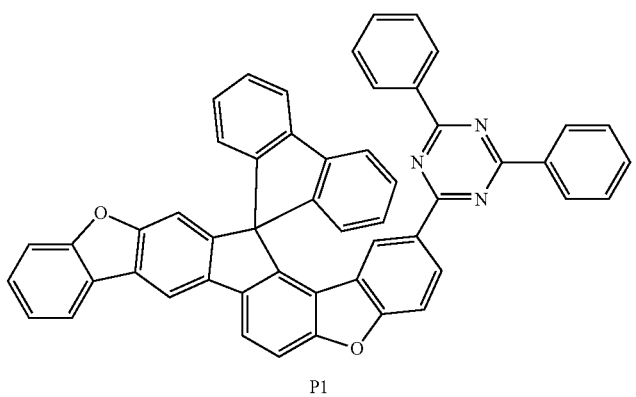

P1

Under nitrogen atmosphere, intermediate compound C1-1 (1 mmol) was added to anhydrous tetrahydrofuran (THF) and stirred at −78° C. to cool the reaction mixture. Then 1.6 M of n-butyl lithium (n-BuLi, 1.1 mmol) was added dropwise, and the reaction was kept at −78° C. for 2 hours. Compound c-1 (1.2 mmol) was slowly added dropwise to the low-temperature reaction solution. After the dropwise addition was complete, the reaction was continued at low temperature for 2 hours and then warmed to room temperature overnight. A small amount of water was added to quench the reaction, dichloromethane/H$_2$O were added for extraction, and the organic phase was collected and dried with anhydrous Na$_2$SO$_4$. The filtrate was collected by suction filtration, and the solvent was removed through rotary evaporation to give the crude product.

Under nitrogen, the above crude product was added to acetic acid (AcOH), stirred, heated and reacted at 120° C. for 2 hours. Then hydrochloric acid was added, and the mixture was heated at this temperature and reacted for 12 hours. The reaction solution was cooled and extracted. The organic phase was collected, the solvent was removed through rotary evaporation, and the residue was purified by column chromatography to give the target product P1 (with a yield of 68%).

MALDI-TOF MS (m/z): $C_{52}H_{29}N_3O_2$, calculated value: 727.23, measured value: 727.45.

Elemental analysis (%): calculated value: C, 85.81; H, 4.02; N, 5.77; measured value: C, 85.80; H, 4.01; N, 5.79.

Example 2

An organic compound P73 is provided, and the structure of the organic compound P73 is as follows:

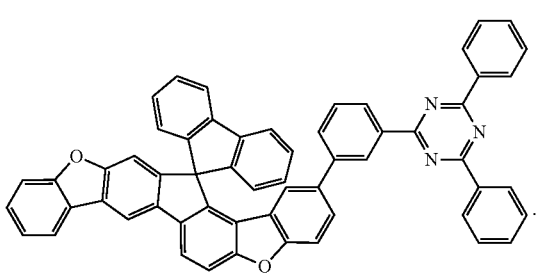

P73

The preparation method of the organic compound P73 differs from the preparation method in Example 1 only in that reactant b-1 in Step (2) was replaced with reactant b-2

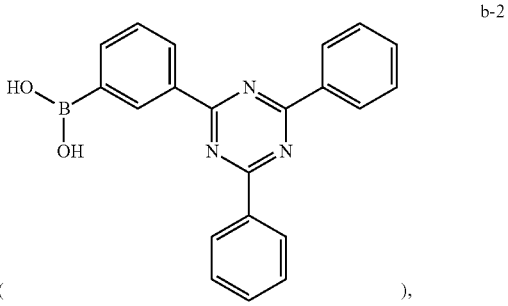 [SMILES: OB(O)c1cccc(-c2nc(-c3ccccc3)nc(-c3ccccc3)n2)c1]

b-2 while other raw materials and process parameters are the same as those in Example 1. The target product P73 was given, with a yield of 70%.

MALDI-TOF MS (m/z): $C_{58}H_{33}N_3O_2$, calculated value: 803.26, measured value: 803.46.

Elemental analysis (%): calculated value: C, 86.65; H, 4.14; N, 5.23; measured value: C, 86.64; H, 4.13; N, 5.25.

Example 3

An organic compound P77 is provided, and the structure of the organic compound P77 is as follows:

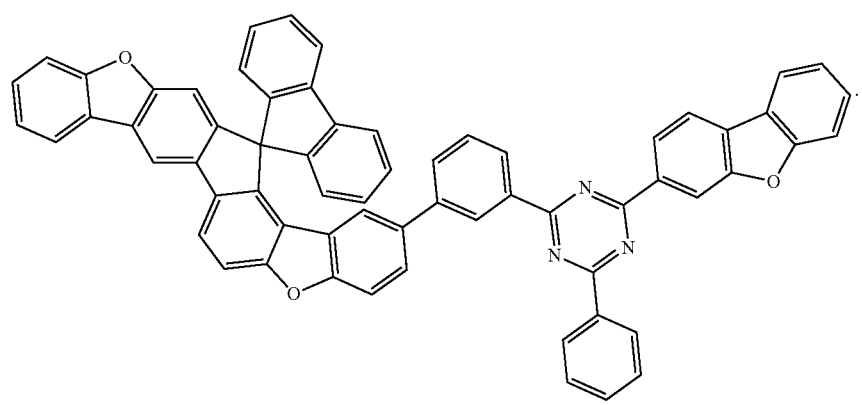

P77

The preparation method of the organic compound P77 differs from the preparation method in Example 1 only in that reactant b-1 in Step (2) was replaced with reactant b-3

(

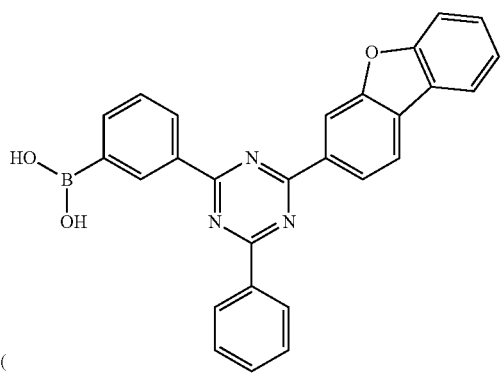

b-3

), while other raw materials and process parameters are the same as those in Example 1. The target product P77 was given, with a yield of 67%.

MALDI-TOF MS (m/z): $C_{64}H_{35}N_3O_3$, calculated value: 893.27, measured value: 893.50.

Elemental analysis (%): calculated value: C, 85.98; H, 3.95; N, 4.70; measured value: C, 85.97; H, 3.94; N, 4.73.

Example 4

An organic compound P31 is provided, and the structure of the organic compound P31 is as follows:

P31

The preparation method includes the steps described below.

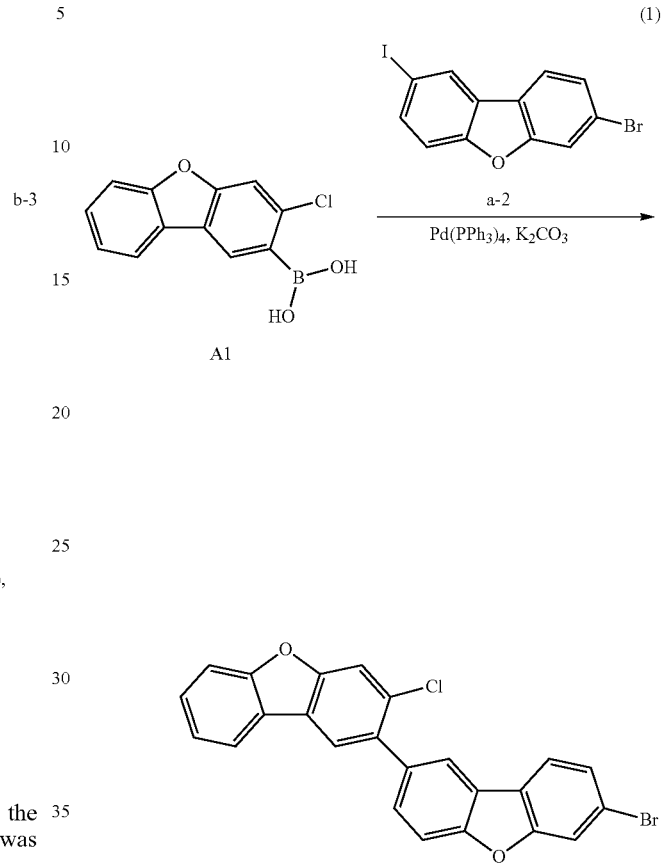

Under nitrogen atmosphere, a reaction solvent consisting of toluene, ethanol and water in the ratio of 7:2:1 was added to a reaction flask, then $K_2CO_3$ (10 mmol, aq), intermediate reactant A1 (5 mmol), reactant a-2 (5 mmol), and $Pd(PPh_3)_4$ (0.25 mmol) were added in sequence, and the mixture was heated to 80° C. and reacted for overnight. After the reaction was complete, the reaction solution was cooled to room temperature, dichloromethane/$H_2O$ were added for extraction, and the collected organic phases were dried with anhydrous $Na_2SO_4$. The filtrate was collected by suction filtration, the solvent was removed through rotary evaporation, and the residue was purified by column chromatography to give intermediate B2 (with a yield of 74%).

MALDI-TOF MS (m/z): $C_{24}H_{12}BrClO_2$, calculated value: 445.97, measured value: 446.20.

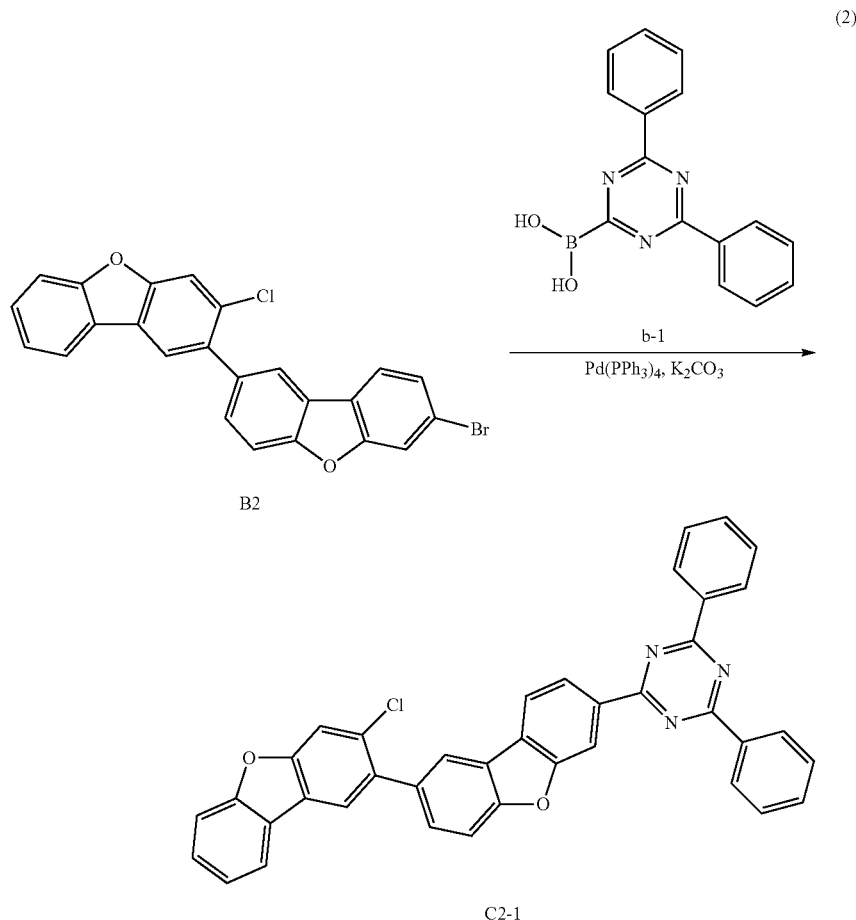

Under nitrogen atmosphere, a reaction solvent consisting of toluene, ethanol and water in the ratio of 7:2:1 was added to a reaction flask, then $K_2CO_3$ (8 mmol, aq), intermediate reactant B2 (4 mmol), reactant b-1 (4 mmol), and $Pd(PPh_3)_4$ (0.2 mmol) were added in sequence, and the mixture was heated to 90° C. and reacted for overnight. After the reaction was complete, the reaction was cooled to room temperature, dichloromethane/$H_2O$ were added for extraction, and the collected organic phases were dried with anhydrous $Na_2SO_4$. The filtrate was collected by suction filtration, the solvent was removed through rotary evaporation, and the residue was purified by column chromatography to give intermediate C2-1 (with a yield of 70%).

MALDI-TOF MS (m/z): $C_{39}H_{22}ClN_3O_2$, calculated value: 599.14, measured value: 599.35.

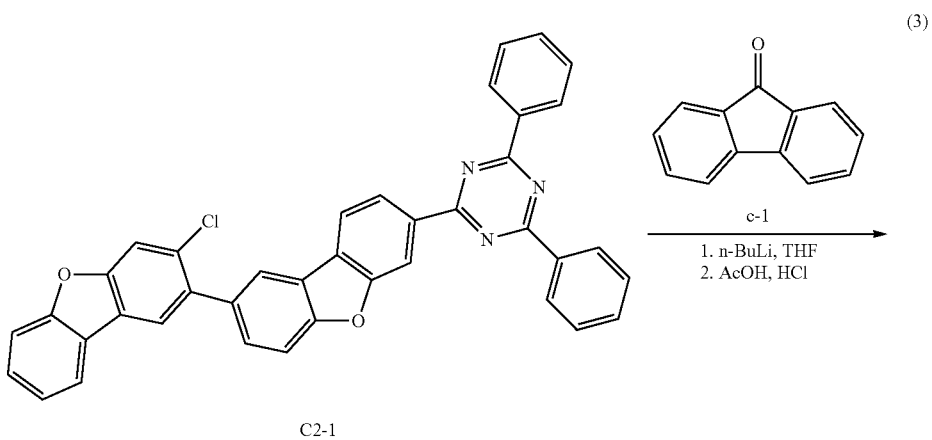

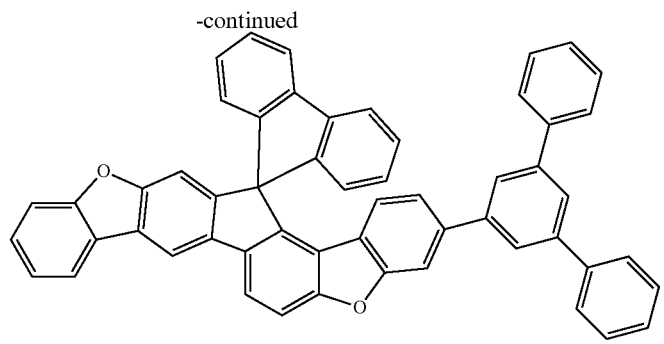

P31

Under nitrogen atmosphere, intermediate compound C2-1 (1 mmol) was added to anhydrous THF and stirred at −78° C. to cool the reaction mixture. Then 1.6 M of n-BuLi (1.1 mmol) was added dropwise, and the reaction was kept at −78° C. for 2 hours. Compound c-1 (1.2 mmol) was slowly added dropwise to the low-temperature reaction solution. After the dropwise addition was complete, the reaction was continued at low temperature for 2 hours and then warmed to room temperature overnight. A small amount of water was added to quench the reaction, dichloromethane/$H_2O$ were added for extraction, and the organic phase was collected and dried with anhydrous $Na_2SO_4$. The filtrate was collected by suction filtration, and the solvent was removed through rotary evaporation to give the crude product.

Under nitrogen, the above crude product was added to acetic acid, stirred, heated and reacted at 120° C. for 2 hours. Then hydrochloric acid was added, and the mixture was heated at this temperature and reacted for 12 hours. The reaction solution was cooled and extracted. The organic phase was collected, the solvent was removed through rotary evaporation, and the residue was purified by column chromatography to give the target product P31 (with a yield of 62%).

MALDI-TOF MS (m/z): $C_{52}H_{29}N_3O_2$, calculated value: 727.23, measured value: 727.50. Elemental analysis (%): calculated value: C, 85.81; H, 4.02; N, 5.77; measured value: C, 85.80; H, 4.01; N, 5.80.

Example 5

An organic compound P55 is provided, and the structure of the organic compound P55 is as follows:

The preparation method of the organic compound P55 differs from the preparation method in Example 4 only in that reactant b-1 in Step (2) was replaced with reactant b-4

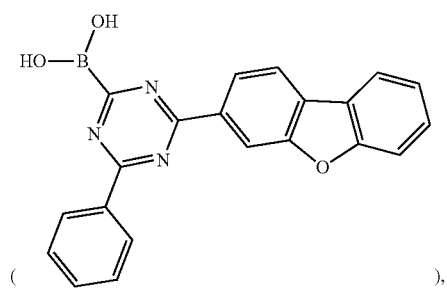

(b-4), while other raw materials and process parameters are the same as those in Example 4. The target product P55 was given, with a yield of 60%.

MALDI-TOF MS (m/z): $C_{58}H_{31}N_3O_3$, calculated value: 817.24, measured value: 817.45.

Elemental analysis (%): calculated value: C, 85.17; H, 3.82; N, 5.14; measured value: C, 85.16; H, 3.81; N, 5.16.

Example 6

An organic compound P61 is provided, and the structure of the organic compound P61 is as follows:

P61

The preparation method of the organic compound P61 differs from the preparation method in Example 4 only in that reactant b-1 in Step (2) was replaced with reactant b-2

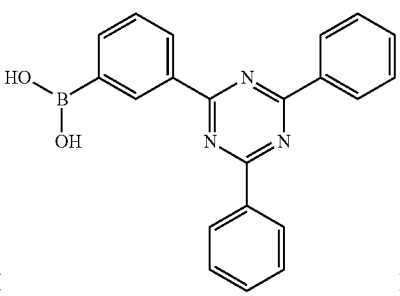

(b-2), while other raw materials and process parameters are the same as those in Example 4. The target product P61 was given, with a yield of 64%.

MALDI-TOF MS (m/z): $C_{58}H_{33}N_3O_2$, calculated value: 803.26, measured value: 803.55.

Elemental analysis (%): calculated value: C, 86.65; H, 4.14; N, 5.23; measured value: C, 86.64; H, 4.13; N, 5.25.

Example 7

An organic compound P62 is provided, and the structure of the organic compound P62 is as follows:

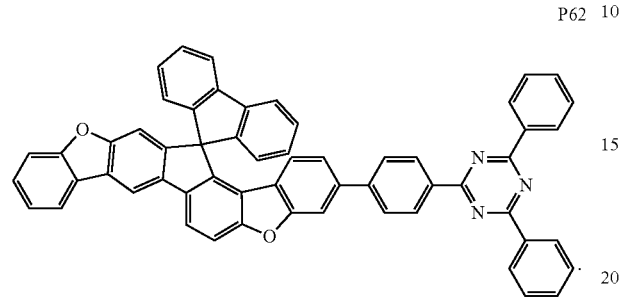

The preparation method of the organic compound P62 differs from the preparation method in Example 4 only in that reactant b-1 in Step (2) was replaced with reactant b-5

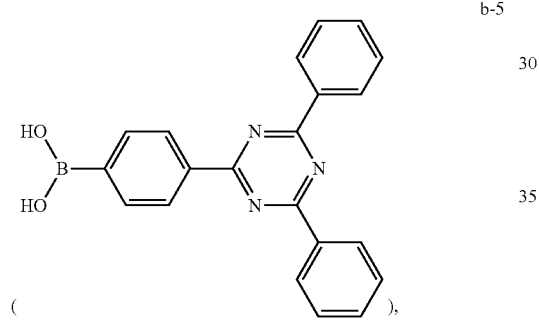

while other raw materials and process parameters are the same as those in Example 4. The target product P62 was given, with a yield of 65%.

MALDI-TOF MS (m/z): $C_{58}H_{33}N_3O_2$, calculated value: 803.26, measured value: 803.50.

Elemental analysis (%): calculated value: C, 86.65; H, 4.14; N, 5.23; measured value: C, 86.64; H, 4.13; N, 5.25.

Example 8

An organic compound P131 is provided, and the structure of the organic compound P131 is as follows:

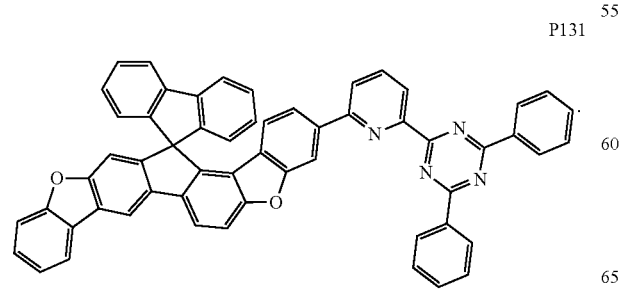

The preparation method of the organic compound P131 differs from the preparation method in Example 4 only in that reactant b-1 in Step (2) was replaced with reactant b-6

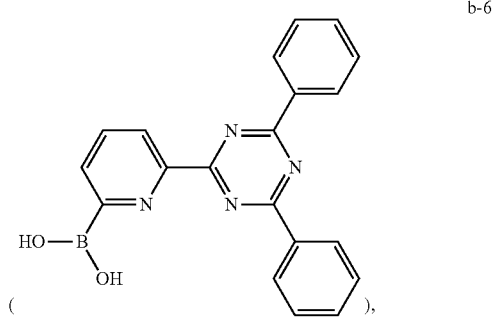 [SMILES: OB(O)c1cccc(-c2nc(-c3ccccc3)nc(-c3ccccc3)n2)n1]

while other raw materials and process parameters are the same as those in Example 4. The target product P131 was given, with a yield of 66%.

MALDI-TOF MS (m/z): $C_{57}H_{32}N_4O_2$, calculated value: 804.25, measured value: 804.45.

Elemental analysis (%): calculated value: C, 85.06; H, 4.01; N, 6.96; measured value: C, 85.05; H, 4.00; N, 6.70.

Example 9

An organic compound P134 is provided, and the structure of the organic compound P134 is as follows:

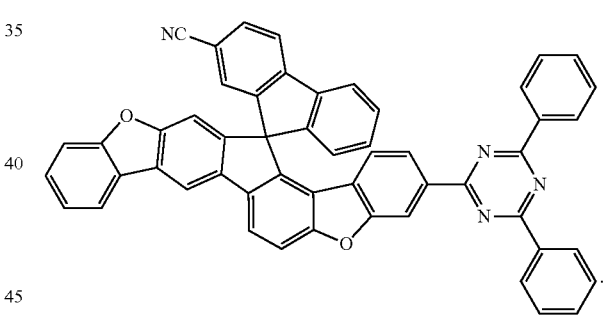

The preparation method of the organic compound P134 differs from the preparation method in Example 4 only in that compound c-1 in Step (3) was replaced with compound c-2

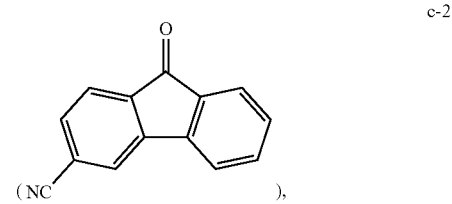 [SMILES: N#Cc1ccc2c(c1)-c1ccccc1C2=O]

while other raw materials and process parameters are the same as those in Example 4. The target product P134 was given, with a yield of 62%.

MALDI-TOF MS (m/z): $C_{53}H_{28}N_4O_2$, calculated value: 752.22, measured value: 752.51.

Elemental analysis (%): calculated value: C, 84.56; H, 3.75; N, 7.44; measured value: C, 84.55; H, 3.74; N, 7.47.

Example 10

An organic compound P89 is provided, and the structure of the organic compound P89 is as follows:

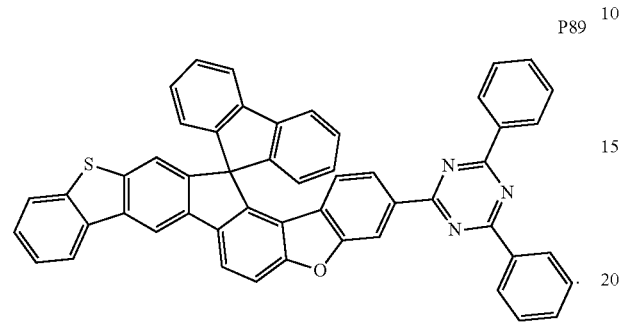

P89

The preparation method of the organic compound P89 differs from the preparation method in Example 4 only in that intermediate reactant A1 in Step (1) was replaced with intermediate reactant A2

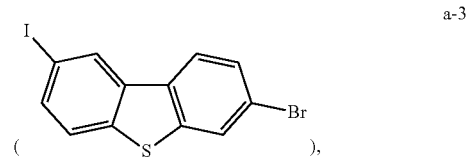

A2 while other raw materials and process parameters are the same as those in Example 4. The target product P89 was given, with a yield of 64%.

MALDI-TOF MS (m/z): $C_{52}H_{29}N_3OS$, calculated value: 743.20, measured value: 743.50.

Elemental analysis (%): calculated value: C, 83.96; H, 3.93; N, 5.65; measured value: C, 83.95; H, 3.92; N, 5.68.

Example 11

An organic compound P101 is provided, and the structure of the organic compound P101 is as follows:

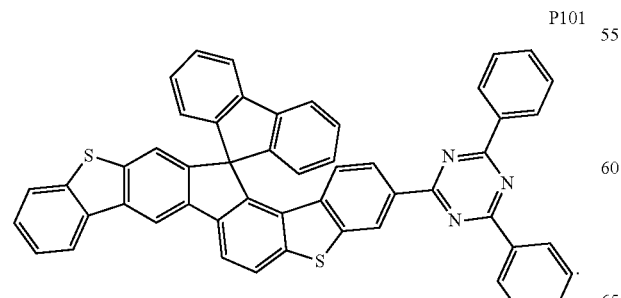

P101

The preparation method of the organic compound P101 differs from the preparation method in Example 4 only in that intermediate reactant A1 in Step (1) was replaced with intermediate reactant A2

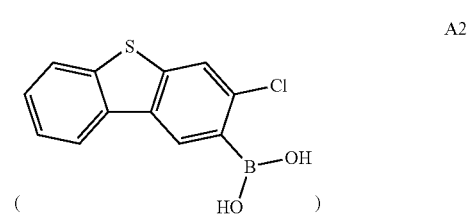 [SMILES: OB(O)c1cc2c(cc1Cl)sc1ccccc12]

A2 and reactant a-2 was replaced with reactant a-3 a-3 while other raw materials and process parameters are the same as those in Example 4. The target product P101 was given, with a yield of 63%.

MALDI-TOF MS (m/z): $C_{52}H_{29}N_3S_2$, calculated value: 759.18, measured value: 759.45.

Elemental analysis (%): calculated value: C, 82.19; H, 3.85; N, 5.53; measured value: C, 82.18; H, 3.84; N, 5.55.

Example 12

An organic compound P113 is provided, and the structure of the organic compound P113 is as follows:

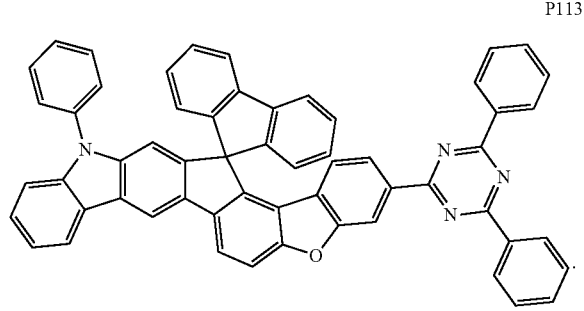 [SMILES: c1ccc(-c2nc(-c3ccccc3)nc(-c3ccc4c(c3)oc3ccc5c(c34)C3(c4ccccc4-c4ccccc43)c3cc4c(cc3-5)c3ccccc3n4-c3ccccc3)n2)cc1]

P113

The preparation method of the organic compound P113 differs from the preparation method in Example 4 only in that intermediate reactant A1 in Step (1) was replaced with intermediate reactant A3

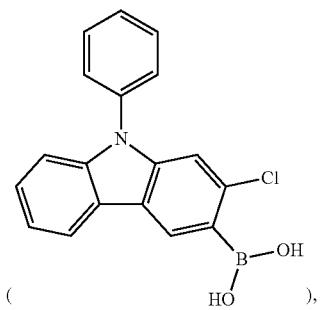

while other raw materials and process parameters are the same as those in Example 4. The target product P113 was given, with a yield of 61%.

MALDI-TOF MS (m/z): $C_{58}H_{34}N_4O$, calculated value: 802.27, measured value: 802.56.

Elemental analysis (%): calculated value: C, 86.76, H 4.27, N ,6.98; measured value: C, 86.75, H, 4.25, N, 7.01.

Simulation Calculations of Compounds:

Based on density functional theory (DFT), the distribution and energy levels of molecular frontier orbital HOMO and LUMO of the organic compounds provided by the present disclosure were optimized and calculated by using a Guassian 09 package (Guassian Inc.) at a calculation level of B3LYP/6-31G(d). Meanwhile, based on time-dependent density functional theory (TD-DFT), the lowest singlet energy level $E_{S1}$ and the lowest triplet energy level $E_{T1}$ of molecules of the compounds were simulated and calculated. Results are shown in Table 1.

TABLE 1

|  | Organic compound | HOMO (eV) | LUMO (eV) | $E_{S1}$ (eV) | $E_{T1}$ (eV) |
|---|---|---|---|---|---|
| Example 1 | P1 | −5.45 | −1.77 | 3.34 | 2.90 |
| Example 2 | P73 | −5.41 | −1.70 | 3.39 | 2.92 |
| Example 3 | P77 | −5.42 | −1.73 | 3.37 | 2.91 |
| Example 4 | P31 | −5.47 | −1.92 | 3.16 | 2.72 |
| Example 5 | P55 | −5.48 | −1.94 | 3.16 | 2.72 |
| Example 6 | P61 | −5.43 | −1.82 | 3.34 | 2.83 |
| Example 7 | P62 | −5.46 | −1.92 | 3.24 | 2.67 |
| Example 8 | P131 | −5.47 | −1.97 | 3.30 | 2.80 |
| Example 9 | P134 | −5.48 | −1.95 | 3.17 | 2.72 |
| Example 10 | P89 | −5.46 | −1.92 | 3.17 | 2.72 |
| Example 11 | P101 | −5.45 | −1.92 | 3.16 | 2.72 |
| Example 12 | P113 | −5.41 | −1.91 | 3.16 | 2.71 |

As can be seen from Table 1, the organic compounds of the present disclosure had a deep LUMO energy level (−1.70 eV to −1.97 eV), which can reduce the potential barrier for electron transport, improve the electron injection ability, and effectively reduce the voltage of OLED devices; the organic compounds had a deep HOMO energy level (−5.41 eV to −5.48 eV), which can effectively block holes and make more holes and electrons recombine in the light-emitting region; meanwhile, all the organic compounds had high triplet energy levels ($E_{T1}$≥2.71 eV), which can block excitons in the light-emitting layer and improve the exciton utilization rate. Therefore, the organic compounds provided by the present disclosure can achieve high luminous efficiency. Moreover, the organic compounds also have a spiro structure and the molecule has a twisted structure, which can reduce the stacking of molecules, avoid crystallization of molecules, and make the organic compound more stable in the device application.

Application examples in which the organic compounds provided by the present disclosure are applied to the OLED devices are described below for purposes of example.

Application Example 1

An OLED device is provided. The OLED device sequentially includes a substrate, an anode (indium tin oxide, ITO), a hole injection layer, a hole transport layer, an electron blocking layer, a light-emitting layer, a hole blocking layer, an electron transport layer, an electron injection layer, and a cathode (aluminum electrode). The OLED device is prepared through the following steps:

(1) a glass substrate having an ITO anode (with a thickness of 100 nm) was sonicated in isopropyl alcohol and deionized water for 30 min respectively, and exposed to ozone for about 10 min for cleaning, and then the cleaned glass substrate was installed onto a vacuum deposition device;

(2) compound a was deposited by vacuum evaporation on the ITO anode as the hole injection layer with a thickness of 10 nm;

(3) compound b was deposited by vacuum evaporation on the hole injection layer as the hole transport layer with a thickness of 40 nm;

(4) compound c was deposited by vacuum evaporation on the hole transport layer as the electron blocking layer with a thickness of 10 nm;

(5) compound d and compound e were co-deposited by vacuum evaporation on the electron blocking layer as the light-emitting layer with a thickness of 20 nm, where the doping ratio (mass ratio) of compound d was 5%;

(6) compound f was deposited by vacuum evaporation on the light-emitting layer as the hole blocking layer with a thickness of 10 nm;

(7) the organic compound P1 provided in Example 1 of the present disclosure was deposited by vacuum evaporation on the hole blocking layer as the electron transport layer with a thickness of 30 nm;

(8) LiF was deposited by vacuum evaporation on the electron transport layer as the electron injection layer with a thickness of 2 nm; and (9) an aluminum electrode was deposited by vacuum evaporation on the electron injection layer as the cathode with a thickness of 100 nm to obtain the OLED device.

The structures of compounds used in the OLED device are as follows:

Compound a

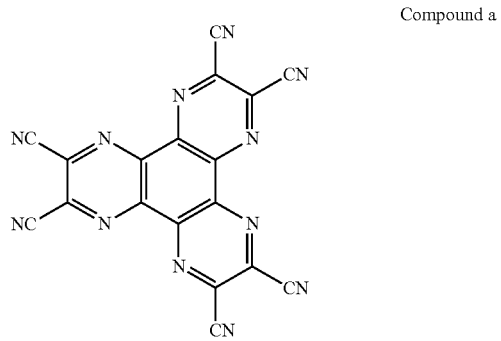

Compound b

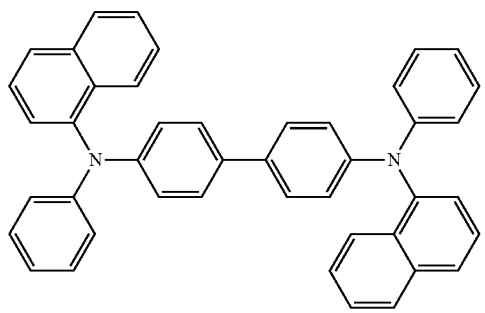

Compound f

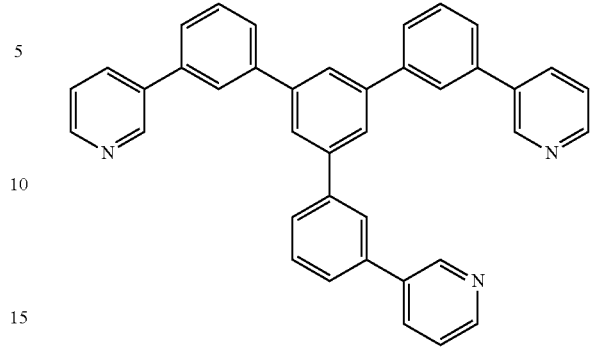

Compound c

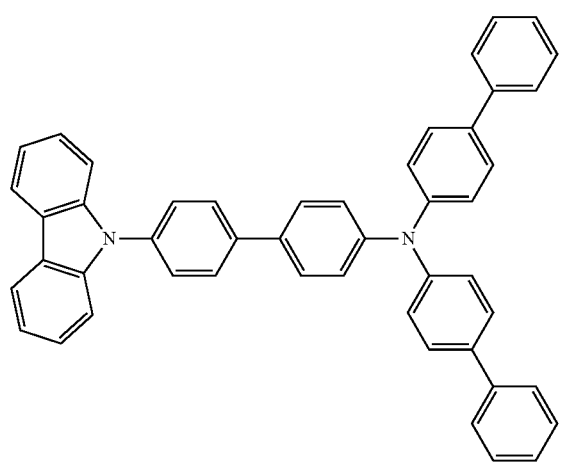

Comparative compound 1

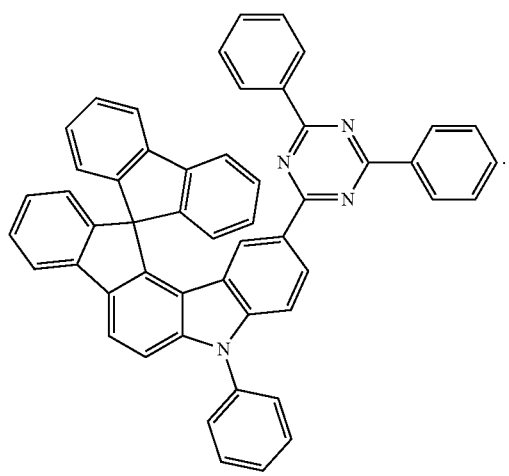

Compound d

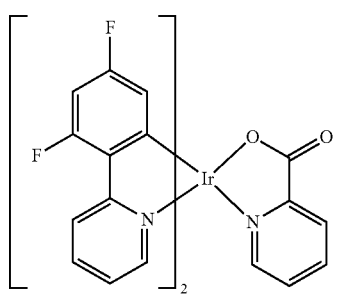

Application Examples 2 to 12 and Comparative Example 1

An OLED device is provided in each of Application Examples 2 to 12 and Comparative Example 1. Each of Application Examples 2 to 12 and Comparative Example 1 differs from Application Example 1 only in that the organic compound P1 in Step (7) was replaced with an equal amount of the organic compounds P73, P77, P31, P55, P61, P62, P131, P134, P89, P101, P113 and comparative compound 1, respectively, while layer structures, materials and preparation methods are the same as those in Application Example 1.

Performance Evaluation of the OLED Devices:

According to the current density and brightness of OLED devices at different voltages, the operating voltage (V, V) and current efficiency (CE, cd/A) at the same current density (10 mA/cm$^2$) are obtained. The lifetime LT95 (in hours, under the testing condition of 500 mA/cm$^2$) is obtained by measuring time when the brightness of the OLED device reaches 95% of its initial brightness. The test data are shown in Table 2.

Compound e

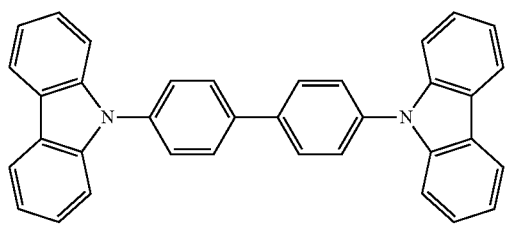

TABLE 2

| OLED device | Electron transport layer material | V (V) | CE (cd/A) | LT95 (h) |
|---|---|---|---|---|
| Application Example 1 | P1 | 4.11 | 14.8 | 63 |
| Application Example 2 | P73 | 4.13 | 14.6 | 64 |
| Application Example 3 | P77 | 4.14 | 14.5 | 62 |
| Application Example 4 | P31 | 4.09 | 15.7 | 64 |
| Application Example 5 | P55 | 4.07 | 15.4 | 66 |
| Application Example 6 | P61 | 4.01 | 16.1 | 69 |
| Application Example 7 | P62 | 4.03 | 15.9 | 67 |
| Application Example 8 | P131 | 4.02 | 15.7 | 63 |
| Application Example 9 | P134 | 4.08 | 15.5 | 61 |
| Application Example 10 | P89 | 4.10 | 15.3 | 63 |
| Application Example 11 | P101 | 4.12 | 15.1 | 62 |
| Application Example 12 | P113 | 4.13 | 14.9 | 60 |
| Comparative Example 1 | Comparative compound 1 | 4.21 | 13.9 | 51 |

As can be seen from Table 2, the organic compounds provided by the present disclosure were applied to the electron transport layers of the OLED devices and the OLED devices had a low working voltage, high luminous efficiency, and long lifetime, where the working voltage was less than or equal to 4.14 V, as low as 4.01 V to 4.14 V, the current efficiency CE was greater than or equal to 14.5 cd/A, and the lifetime LT95 was greater than or equal to 60 hours. Compared with the OLED device in Comparative Example 1, for the OLED device using the compounds of the present disclosure, the working voltage was reduced, and the efficiency and lifetime were improved, which might thanks for the fact that the organic compounds of the present disclosure have a deep LUMO energy level, which can reduce a potential barrier for electron injection and thus reduce the working voltage of the device; the organic compounds have a deep HOMO, which can effectively block holes, widen the light-emitting recombination region, and improve the luminous efficiency of the device; the organic compounds have a high $E_{T1}$, which can effectively block excitons in the light-emitting layer and improve the exciton utilization rate; and the organic compounds provided by the present disclosure have excellent thermal stability and film stability, which is helpful for the stability of the device and improves the lifetime of the device.

What is claimed is:

1. An organic compound, having a structure as shown in Formula I:

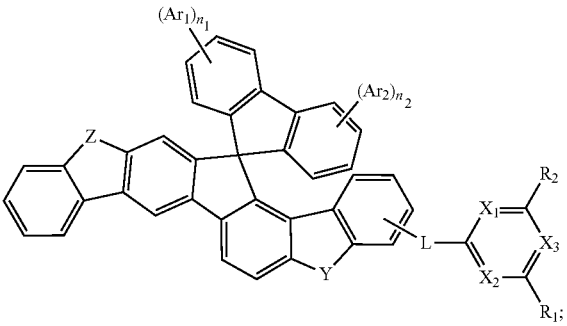

Formula I wherein $X_1$, $X_2$, and $X_3$ are all N;

wherein Y is selected from O, S, $NR_N$ or $CR_{C1}R_{C2}$, and Z is $NR_N$;

wherein L is selected from any one of a single bond, substituted or unsubstituted C6 to C40 arylene, or substituted or unsubstituted C3 to C40 heteroarylene;

wherein $R_1$, $R_2$, R, $R_N$, $R_{C1}$, and $R_{C2}$ are each independently selected from any one of hydrogen, substituted or unsubstituted C1 to C20 linear or branched alkyl, substituted or unsubstituted C6 to C40 aryl, or substituted or unsubstituted C2 to C40 heteroaryl;

wherein $Ar_1$ and $Ar_2$ are each independently selected from any one of deuterium, halogen, cyano, substituted or unsubstituted C1 to C20 linear or branched alkyl, C1 to C20 alkoxy, C1 to C20 alkylthio, substituted or unsubstituted C3 to C20 cycloalkyl, substituted or unsubstituted C6 to C40 aryl, substituted or unsubstituted C2 to C40 heteroaryl, or substituted or unsubstituted C6 to C40 arylamino; and wherein $n_1$ and $n_2$ are each independently selected from integers from 0 to 4.

2. The organic compound according to claim 1, wherein the substituted substituents in L, $R_1$, $R_2$, R, $R_N$, $R_{C1}$, $R_{C2}$, $Ar_1$, and $Ar_2$ are each independently selected from at least one of deuterium, cyano, halogen, unsubstituted or halogenated C1 to C10 linear or branched alkyl, unsubstituted or halogenated C1 to C10 alkoxy, C1 to C10 alkylthio, C6 to C20 aryl, C2 to C20 heteroaryl, or C6 to C18 arylamino.

3. The organic compound according to claim 1, having a structure as shown in Formula II-1 or Formula II-2:

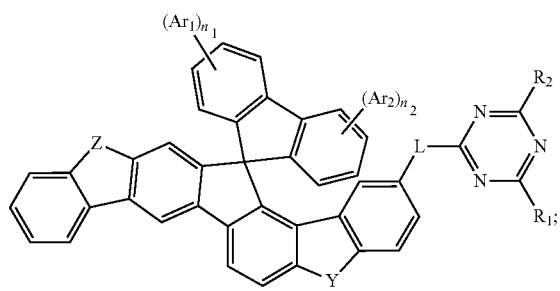

Formula II-1

Formula II-2

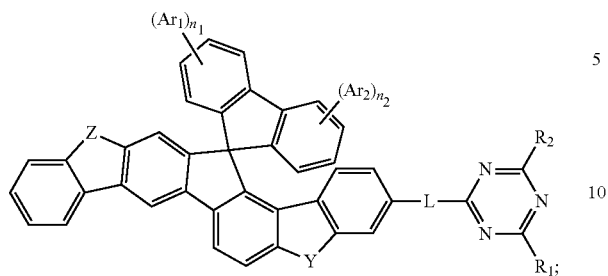

wherein Y, Z, L, $R_1$, $R_2$, $Ar_1$, $Ar_2$, $n_1$, and $n_2$ have the same ranges as defined in Formula I.

4. The organic compound according to claim 1, wherein Y is selected from O, S or $NR_N$, and Z is $NR_N$.

5. The organic compound according to claim 1, wherein $R_N$, $R_{C1}$, and $R_{C2}$ are each independently selected from methyl or phenyl.

6. The organic compound according to claim 1, wherein L is selected from any one of a single bond, phenylene, biphenylene, terphenylene, naphthylene or pyridinylene.

7. The organic compound according to claim 1, wherein $R_1$ and $R_2$ are each independently selected from hydrogen or any one of the following groups:

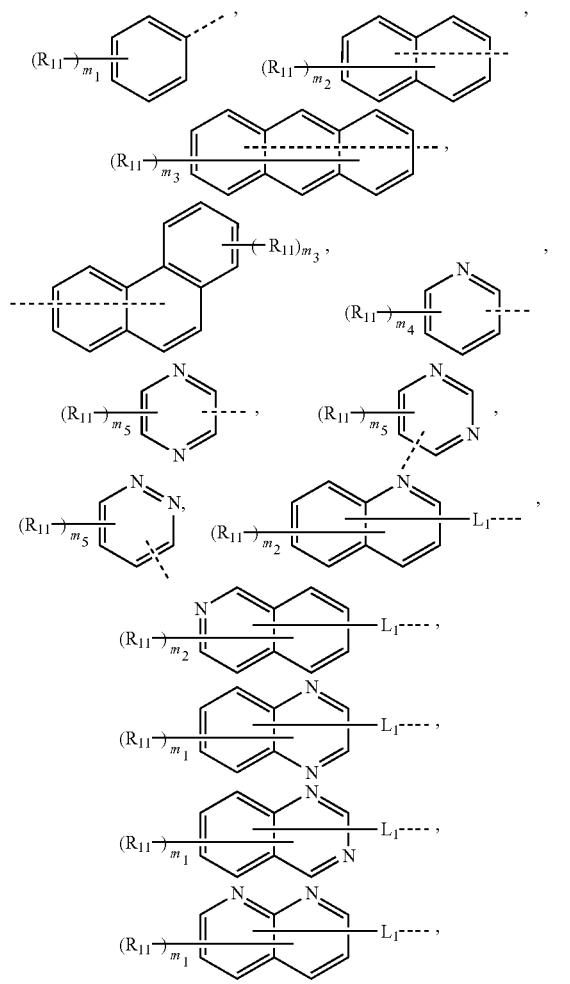

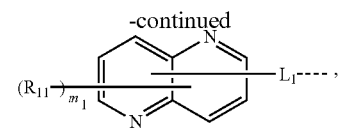

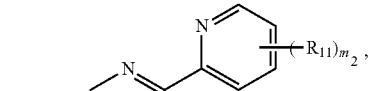

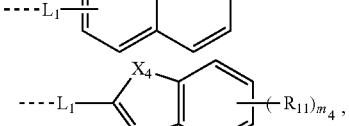

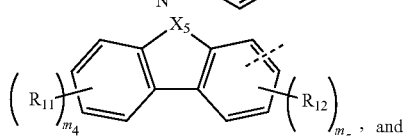

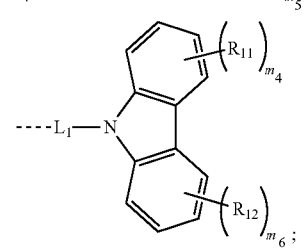

wherein the dashed line represents a linkage site of a group;

wherein $L_1$ is selected from any one of a single bond or substituted or unsubstituted C6 to C20 arylene;

wherein $X_4$ is selected from O, S or $NR_{N1}$;

wherein $X_5$ is selected from O, S, $NR_{N2}$ or $CR_{C3}R_{C4}$;

wherein $R_{N1}$, $R_{N2}$, $R_{C3}$, and $R_{C4}$ are each independently selected from any one of hydrogen, substituted or unsubstituted C1 to C20 linear or branched alkyl, substituted or unsubstituted C6 to C20 aryl, or substituted or unsubstituted C2 to C20 heteroaryl;

wherein $R_{11}$ and $R_{12}$ are each independently selected from any one of deuterium, cyano, halogen, unsubstituted or halogenated C1 to C10 linear or branched alkyl, unsubstituted or halogenated C1 to C10 alkoxy, C1 to C10 alkylthio, C6 to C20 aryl, C2 to C20 heteroaryl, or C6 to C18 arylamino;

wherein $m_1$ is selected from integers from 0 to 5;

wherein $m_2$ is selected from integers from 0 to 6;

wherein $m_3$ is selected from integers from 0 to 9;

wherein $m_4$ and $m_6$ are each independently selected from integers from 0 to 4; and wherein $m_5$ is selected from integers from 0 to 3.

8. The organic compound according to claim 1, wherein $R_1$ and $R_2$ are each independently selected from hydrogen, or any one of the following groups, or any one of the following groups substituted with a substituent:

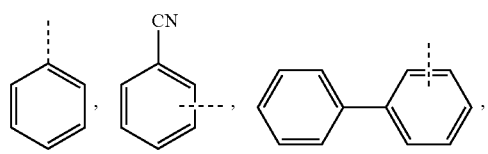

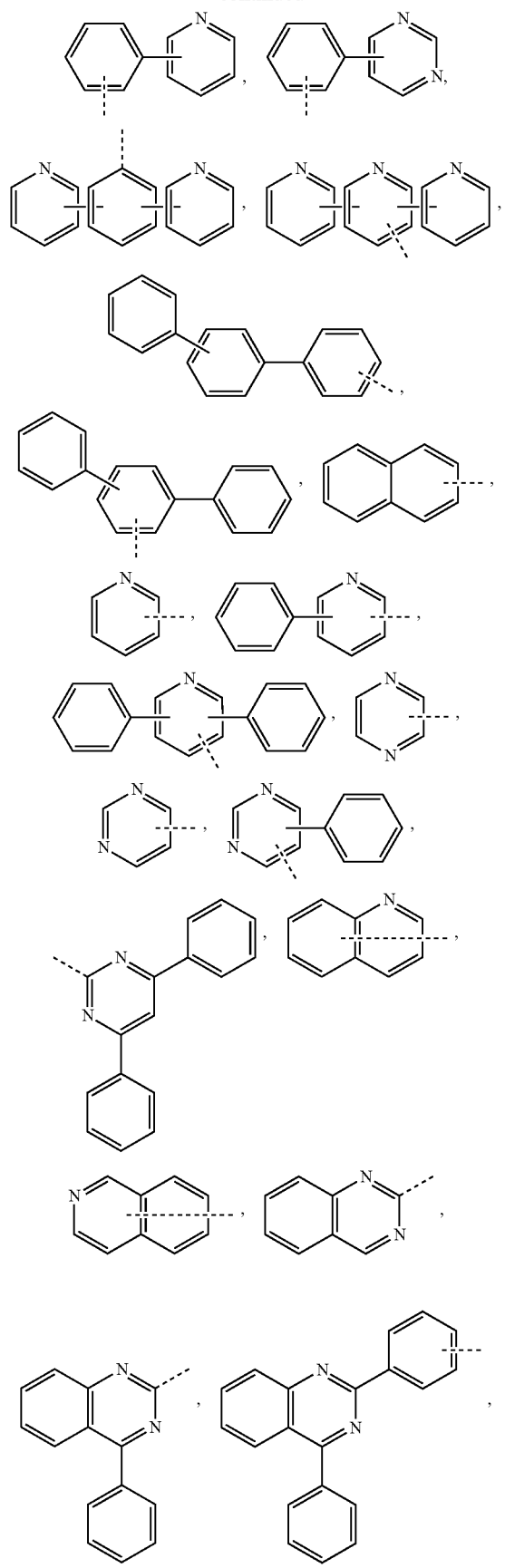
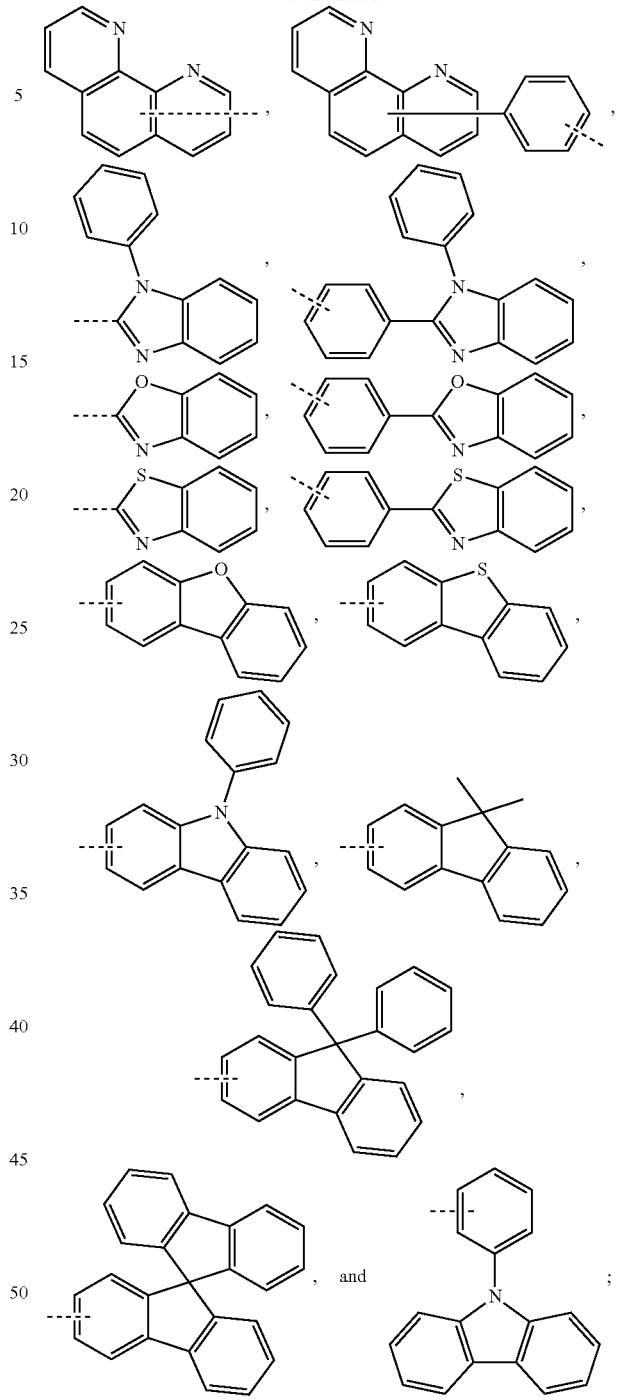

wherein the dashed line represents a linkage site of a group;

wherein the substituted substituents are each independently selected from at least one of deuterium, cyano, halogen, unsubstituted or halogenated C1 to C10 linear or branched alkyl, unsubstituted or halogenated C1 to C10 alkoxy, C1 to C10 alkylthio, C6 to C20 aryl, C2 to C20 heteroaryl, or C6 to C18 arylamino.

9. The organic compound according to claim 1, wherein $Ar_1$ and $Ar_2$ are each independently selected from any one of deuterium, halogen, cyano, phenyl, or unsubstituted or halogenated C1 to C10 linear or branched alkyl.

10. The organic compound according to claim 1, wherein the organic compound is selected from any one of the following compounds:
P112
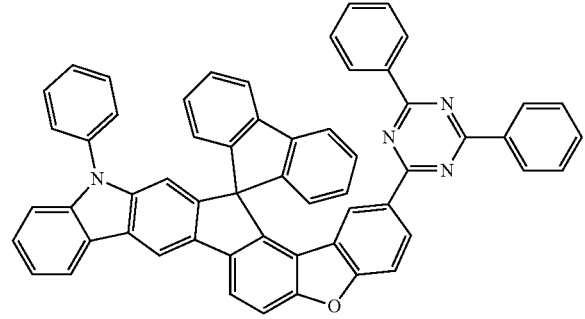
P113
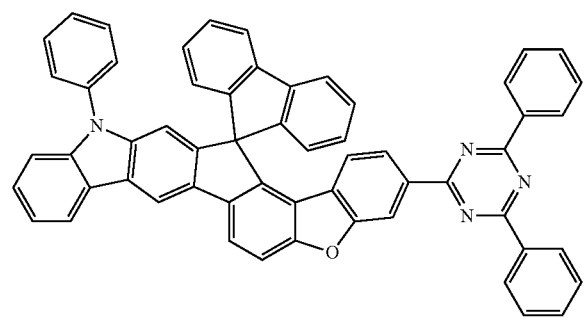
P114
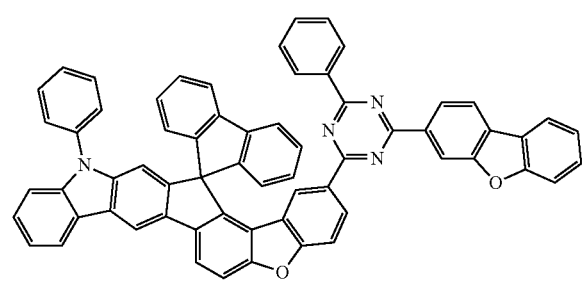
P115
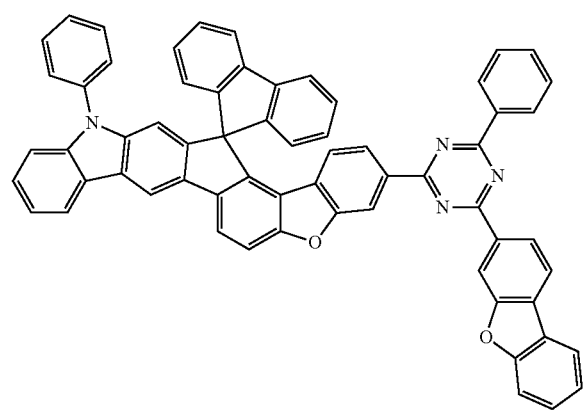
P116
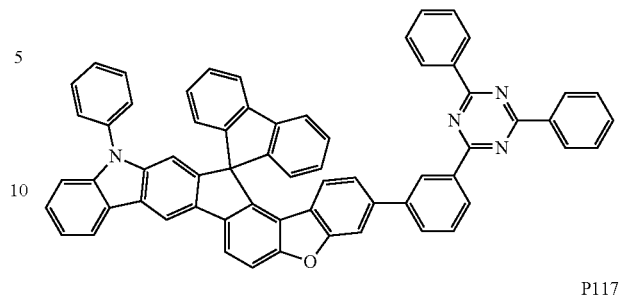
P117
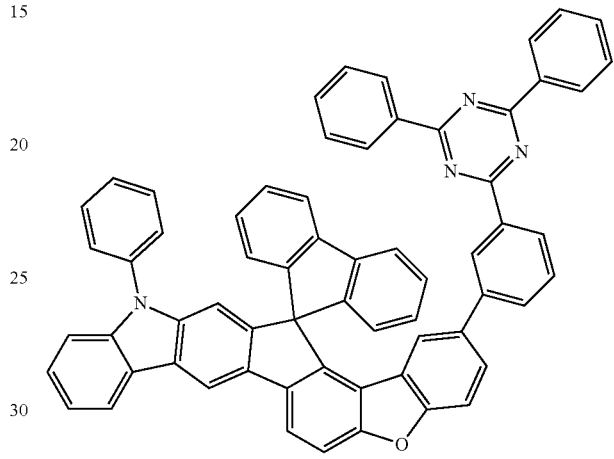
P118
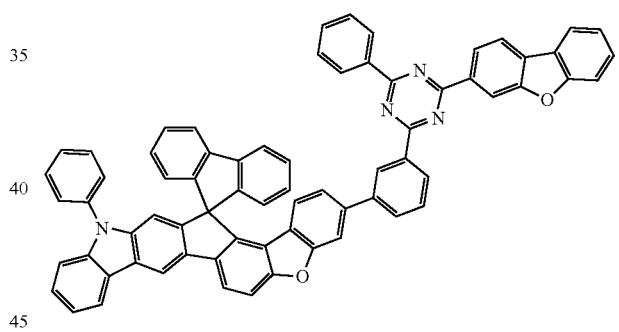
P119

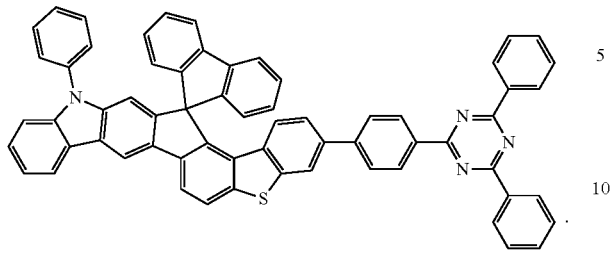

P120

11. An electroluminescent material, comprising the organic compound according to claim 1.

12. An OLED device, comprising an anode, a cathode, and an organic thin film layer located between the anode and the cathode, wherein a material of the organic thin film layer comprises the electroluminescent material according to claim 11.

13. The OLED device according to claim 12, wherein the organic thin film layer comprises an electron transport layer whose material comprises the electroluminescent material.

14. The OLED device according to claim 12, wherein the organic thin film layer comprises a hole blocking layer whose material comprises the electroluminescent material.

15. The OLED device according to claim 12, wherein the organic thin film layer comprises a light-emitting layer whose material comprises the electroluminescent material.

16. A display panel, comprising the OLED device according to claim 12.

* * * * *